(12) United States Patent
Sukumar et al.

(10) Patent No.: US 11,964,054 B2
(45) Date of Patent: *Apr. 23, 2024

(54) FORMULATIONS OF TEGAVIVINT

(71) Applicant: Iterion Therapeutics, Inc., Houston, TX (US)

(72) Inventors: Gowri Sukumar, Spring, TX (US); Drazen Ostovic, Redwood City, CA (US)

(73) Assignee: Iterion Therapeutics, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/106,193

(22) Filed: Feb. 6, 2023

(65) Prior Publication Data

US 2023/0190659 A1    Jun. 22, 2023

Related U.S. Application Data

(63) Continuation-in-part of application No. 17/492,969, filed on Oct. 4, 2021, now Pat. No. 11,602,501, which is a continuation of application No. 17/103,468, filed on Nov. 24, 2020, now Pat. No. 11,571,388.

(51) Int. Cl.
| | |
|---|---|
| *A61K 9/19* | (2006.01) |
| *A61K 9/16* | (2006.01) |
| *A61K 31/4545* | (2006.01) |

(52) U.S. Cl.
CPC .............. *A61K 9/19* (2013.01); *A61K 9/1623* (2013.01); *A61K 9/1641* (2013.01); *A61K 31/4545* (2013.01)

(58) Field of Classification Search
CPC ...... A61K 9/19; A61K 9/1623; A61K 9/1641; A61K 31/4545

See application file for complete search history.

(56) References Cited

U.S. PATENT DOCUMENTS

| | | |
|---|---|---|
| 2017/0029450 A1 | 2/2017 | Vankayalapati et al. |
| 2018/0344713 A1 | 12/2018 | Han et al. |
| 2019/0365729 A1 | 12/2019 | Dykstra et al. |

FOREIGN PATENT DOCUMENTS

WO    2019099836 A1    5/2019

OTHER PUBLICATIONS

Kilinc. Mechanisms and Prevention of Axonal Damage in Response to Mechanical Trauma to Cultured Neurons. Thesis. Drexel University. 206 pages, 2008. (Year: 2008).*
Gibbs et al. Purified Poloxamer 188 for Sickle Cell Vaso-Occlusive Crisis. Annals of Pharmacotherapy 2004, 38(2):320-324. (Year: 2004).*
International Search Report and Written Opinion for corresponding PCT application No. PCT/US2021/060530 dated Feb. 28, 2022.

* cited by examiner

*Primary Examiner* — Robert A Wax
*Assistant Examiner* — Olga V. Tcherkasskaya
(74) *Attorney, Agent, or Firm* — Brown Rudnick LLP; Adam M. Schoen

(57) ABSTRACT

Formulations of tegavivint, methods of making such formulations, and methods of treatment of cancer by administering the formulations.

16 Claims, 30 Drawing Sheets

Optical Microscopy Image of Preparation 1 at 20 Days

Polarized

Bright Field

Optical Microscopy Image of Preparation 4 at 4 Days

Polarized

Bright Field

Microscopy of 5% sorbitol batch (T3M @ 5°C, 400X)

Bright Field Polarized

Microscopy of 5% sorbitol batch (T3M @ 25°C, 400X)

Bright Field Polarized

Microscopy of 5% sorbitol autoclaved batch (T3M @ 5°C, 400X)

Bright Field · Polarized

Microscopy of 5% sorbitol autoclaved batch (T3M @ 25°C, 400X)

Bright Field · Polarized

FORMULATIONS OF TEGAVIVINT

FIELD OF THE INVENTION

The present invention relates generally to formulations of tegavivint and methods of making such formulations.

BACKGROUND OF THE INVENTION

Cancer is the second leading cause of death in the United States. It presents complex challenges for the development of new therapies. Cancer is characterized by the abnormal growth of malignant cells that have undergone a series of genetic changes that lead to growth of tumor mass and metastatic properties.

Beta-catenin (β-catenin) is part of a complex of proteins that constitute adherens junctions (AJs). AJs are necessary for the creation and maintenance of epithelial cell layers by regulating cell growth and adhesion between cells. β-catenin also anchors the actin cytoskeleton and may be responsible for transmitting the contact inhibition signal that causes cells to stop dividing once the epithelial sheet is complete.

Wnt/β-catenin pathway has been shown to play a role in cancer. Aberrant β-catenin signaling plays an important role in tumorigenesis. In particular, colorectal cancer is estimated to have greater than 80% mutations in the β-catenin pathway, leading to unregulated oncogenic signaling. Aberrant β-catenin signaling has been shown to be involved in various cancer types, including but not limited to, melanoma, breast, lung, colon, liver, gastric, myeloma, multiple myeloma, chronic myelogenous leukemia, chronic lymphocytic leukemia, T-cell non-Hodgkin lymphomas, colorectal and acute myeloid leukemia (AML) cancers. Further, aberrant Wnt/β-catenin signaling has been found in a large number of other disorders, including osteoporosis, osteoarthritis, polycystic kidney disease, diabetes, schizophrenia, vascular disease, cardiac disease, hyperproliferative disorders, neurodegenerative diseases, and fibrotic diseases including but not limited to idiopathic pulmonary fibrosis (IPF), Dupuytren's contracture, Nonalcoholic steatohepatitis (NASH), and others. Myeloproliferative neoplasms (MPNs) are a closely related group of hematological malignancies in which the bone marrow cells that produce the body's blood cells develop and function abnormally. The three main myeloproliferative neoplasms are Polycythemia Vera (PV), Essential Thrombocythemia (ET) and Primary Myelofibrosis (PMF). A gene mutation in JAK2 is present in most PV patients and 50% of ET and PMF patients. The beta catenin pathway is activated in MPN in many cases and required for survival of these cells.

Tegavivint and related compounds are described, for example, in U.S. Pat. No. 8,129,519. Tegavivint has the following structural formula:

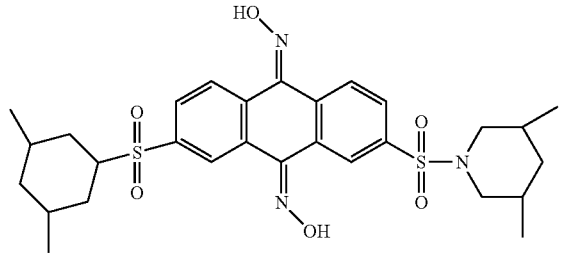

The molecular formula of tegavivint is $C_{28}H_{36}N_4O_6S_2$.
The molecular mass of tegavivint is 588.20763 amu.

There is a need in the art to provide formulations of tegavivint, including but not limited to stable lyophilized formulations of tegavivint, wherein the formulations, when reconstituted, allow administration via different routes of administration, including but not limited to, parenteral and via inhalation, and are stable to be suitable for a clinical study and treatment of various diseases which are treatable with tegavivint.

SUMMARY OF THE INVENTION

It has been very challenging and difficult to develop a stable formulation of tegavivint. A large number of formulations were developed and tested; however, they had poor bioavailability and/or proved unstable upon storage, and/or turned to be highly toxic. It was challenging and difficult to obtain formulations that retained good cake integrity, re-suspended readily and demonstrated chemical stability over time.

The inventors have unexpectedly and surprisingly discovered that a stable formulation can be made when it is produced utilizing Form I or Form IV polymorphs of tegavivint as starting material, when the starting material is subjected to high energy milling at an elevated temperature of about 60° C. Form I and Form IV polymorphs are described in detail in U.S. patent application Ser. No. 17/037,287, the contents of which are hereby incorporated by reference in their entirety.

In yet another embodiment, the invention provides a nanosuspension of tegavivint wherein the nanosuspension was prepared by a process comprising using either Form I or Form IV as the starting material and milling performed at a temperature of between about 40° C. and about 60° C., most preferably at about 60° C.

In one embodiment, if the milling process is done at temperature of less than about 60° C., the nanosuspension further undergoes the annealing process at or above 60° C.

In one embodiment, the invention provides a formulation comprising particles of Form I or Form IV polymorph of tegavivint or a pharmaceutically acceptable salt, ester, amide, stereoisomer or geometric isomer thereof; wherein the particles have an effective D90 of less than or equal to 0.2 micron when measured using laser diffraction, and wherein the formulation was prepared by high energy agitator milling at a temperature of between about 40° C. and about 60° C.

In one embodiment, the formulation may be lyophilized.

In one embodiment, the particles have an effective D90 of less than or equal to 0.2 micron when measured using laser diffraction.

In one embodiment, the particles have an effective D50 of less than or equal to 0.12 micron when measured using laser diffraction.

In one embodiment, the particles have an effective D10 of less than or equal to 0.1 micron when measured using laser diffraction.

In some embodiments, the effective average particle size of tegavivint is about 4900 nm, about 4800 nm, about 4700 nm, about 4600 nm, about 4500 nm, about 4400 nm, about 4300 mm, about 4200 nm, about 4100 nm, about 4 microns, about 3900 nm, about 3800 nm, about 3700 nm, about 3600 nm, about 3500 nm, about 3400 mm, about 3300 nm, about 3200 nm, about 3100 nm, about 3 microns, about 2900 mm, about 2800 nm, about 2700 nm, about 2600 nm, about 2500 nm, about 2400 nm, about 2300 nm, about 2200 nm, about 2100 nm, about 2000 nm, about 1900 nm, about 1800 nm, about 1700 nm, about 1600 nm, about 1500 nm, about 1400 nm, about 1300 nm, about 1200 nm, about 1100 nm, about 1000 nm, about 900 nm, about 800 nm, about 700 nm, about 600 nm, about 500 nm, about 400 nm, or about 300 nm.

Further, in some embodiments, the effective average particle size of the compounds is less than 900 nm, more preferably less than 500 nm, and even more preferably, less than 300 nm.

The provided formulations are stable for therapeutic utility.

In one embodiment, the lyophilized formulations of the invention are anhydrous.

In one embodiment, the formulations, including lyophilized formulations, of the invention are stored in a dry atmosphere.

The storage temperature for the formulations of the invention can be about −20° C., about 5° C., or about 25° C.

In one embodiment, the invention provides a stable formulation comprising particles of tegavivint; wherein the particles have an effective D50 of less than or equal to 500 nm and D90 of less than or equal to 1.0 micrometer (μm) when measured using laser diffraction, wherein the formulation comprises tegavivint, a poloxamer, and one or more stabilizer selected from the group consisting of sucrose, trehalose and sorbitol, and wherein the formulation is prepared by high energy agitator milling at a temperature of between about 40° C. and about 60° C.

In one embodiment, tegavivint concentration in a formulation is 2% (20 mg/mL).

In one embodiment, tegavivint concentration in a formulation is 2.5% (25 mg/mL).

In another embodiment, tegavivint concentration in a formulation is 5% (50 mg/mL).

In one embodiment, the poloxamer is Poloxamer 188.

In one embodiment, the poloxamer concentration in a formulation is 6 mg/mL.

In another embodiment, the poloxamer concentration in a formulation is 12.5 mg/mL.

In one embodiment, the sucrose concentration in a formulation is 100 mg/mL.

In another embodiment, the trehalose concentration in a formulation is 100 mg/mL.

In one embodiment, the sorbitol concentration in a formulation is 50 mg/mL.

In one embodiment, the invention provides a stable formulation comprising particles of tegavivint; wherein the particles have an effective D50 of less than or equal to 500 nm and D90 of less than or equal to 1.0 micrometer (μm) when measured using laser diffraction, wherein the formulation is a product of lyophilization of a pre-lyophilized formulation comprising tegavivint, a poloxamer, and one or more stabilizer selected from the group consisting of sucrose, trehalose and sorbitol.

In one embodiment, tegavivint concentration in a pre-lyophilized formulation is 2% (20 mg/mL).

In one embodiment, tegavivint concentration in a pre-lyophilized formulation is 2.5% (25 mg/mL).

In another embodiment, tegavivint concentration in a pre-lyophilized formulation is 5% (50 mg/mL).

In one embodiment, the poloxamer is Poloxamer 188.

In one embodiment, the poloxamer concentration in a formulation is between about 6 mg/mL and about 12 mg/mL.

In one embodiment, the poloxamer concentration in a formulation is about 6 mg/mL.

In one embodiment, the poloxamer concentration in a formulation is about 12.5 mg/mL.

In one embodiment, the sorbitol concentration is about 50 mg/mL.

In one embodiment, the poloxamer concentration in a pre-lyophilized formulation is about 6 mg/mL.

In another embodiment, the poloxamer concentration in a pre-lyophilized formulation is about 12 mg/mL.

In one embodiment, the sucrose concentration in a pre-lyophilized formulation is about 100 mg/mL.

In another embodiment, the trehalose concentration in a pre-lyophilized formulation is about 100 mg/mL.

In one embodiment, the sorbitol concentration in a pre-lyophilized formulation is about 50 mg/mL.

In one embodiment, the formulation is prepared by a process comprising high energy agitator milling at a temperature of about 60° C.

In one embodiment, the tegavivint in the formulation is Form I polymorph.

In one embodiment, the formulations of the invention are stable for three months, six months, twelve months or eighteen months at storage at a temperature of between 5° C. and 25° C.

In one embodiment, the formulation is autoclaved prior to lyophilization.

In one embodiment, the lyophilization process comprises freezing the formulation to about −40° C., a primary drying step at −30° C. and a secondary drying step at about −10° C.

The invention also includes pre-lyophilized formulations of tegavivint.

In one embodiment, the pre-lyophilized formulation is prepared by a process comprising ball milling at a temperature of about 60° C.

In one embodiment, the pre-lyophilized formulation is prepared by a process comprising high energy milling at a temperature of about 60° C.

In one embodiment, the tegavivint in the pre-lyophilized formulation is Form I polymorph.

In one embodiment, the formulations of the invention are stable for three months, six months, twelve months or eighteen months at storage at a temperature of between 5° C. and 25° C.

In a preferred embodiment, the formulations of the invention exhibit long term stability.

In one embodiment, the formulations of the invention, including but not limited to lyophilized formulations of the invention, when reconstituted, may be formulated: (a) into a dosage form selected from the group consisting of tablets, and capsules; (b) into a dosage form selected from the group consisting of controlled release formulations, fast melt formulations, delayed release formulations, extended release formulations, pulsatile release formulations, and mixed immediate release and controlled release formulations; (c) into a dosage form suitable for inhalation or parenteral administration, including intramuscular, subcutaneous, intravenous and intradermal injection; (d) any combination of (a), (b) and (c).

In one embodiment, the formulations of the invention, including but not limited to the lyophilized formulations of the invention, when administered to rats via intravenous (IV) infusion at 15.5 mg/mL concentration, result in one or more of the following values: $C_{max}$ of at least about 50,000 ng/mL in plasma; at least about 200 ng/g in brain; at least about 2900 ng/g in heart; at least about 3700 ng/g in kidney; at least about 35000 ng/g in lungs; at least about 400 ng/g in pectoral thigh muscle; at least about 360000 ng/g in spleen; at least about 470 ng/g in visceral fat; and at least about 237,000 ng/g in liver.

In another embodiment, the formulations of the invention, including but not limited to the lyophilized formulations of the invention, when administered to rats via IV infusion at 15.5 mg/mL concentration, result in one or more of the following values: $AUC_{last}$ of at least about 68,000 hr·ng/mL in plasma; at least about 1800 hr·ng/g in brain; at least about 45000 hr·ng/g in heart; at least about 58000 hr·ng/g in kidney; at least about 450000 hr·ng/g in lungs; at least about 5700 hr·ng/g in pectoral thigh muscle; at least about 4800000 hr·ng/g in spleen; at least about 4000 hr·ng/g in visceral fat; and at least about 3,600,000 hr·ng/g in liver.

In another embodiment, the formulations of the invention, including but not limited to the lyophilized formulations of the invention, when administered to rats via IV infusion at 15.5 mg/mL concentration, result in one or more of the following values: $T_{max}$ of about 0.08 hr or less in plasma; about 0.5 hr or less in brain; about 1 hr or less in heart; about 0.5 hr or less in kidney; about 0.5 hr or less in lungs; about 0.5 hr or less in pectoral thigh muscle; about 0.5 hr or less in spleen; about 1 hr or less in visceral fat; and about 1 hr or less in liver.

The pharmaceutical formulations of the invention can further comprise one or more pharmaceutically acceptable excipients, carriers, or a combination thereof.

In another embodiment, the invention provides a method of preventing, treating or ameliorating cancer or tumor metastasis in a mammal in need thereof comprising administering to said mammal an effective amount of the formulations of the invention.

The method of administering is not limited to any specific route of administration, and includes, but is not limited to, intravenous, parenteral, oral, inhalation (including aerosolized delivery), buccal, intranasal, rectal, intra-lesional intraperitoneal, intradermal, transdermal, subcutaneous, intra-arterial, intracardiac, intraventricular, intracranial, intratracheal, intrathecal administration, intramuscular injection, intravitreous injection, and topical application methods.

In another embodiment, the method of preventing, treating or ameliorating cancer or tumor metastasis in a mammal in need thereof can include administering an additional anti-cancer agent and/or cancer therapy (for example, cancer vaccines, anti-cancer adoptive cell therapies and radio therapies).

In one embodiment, the additional anti-cancer agent is selected from the group consisting of antimitotic agents, antimetabolite agents, histone deacetylase (HDAC) inhibitors, proteosome inhibitors, immunotherapeutic agents, Fms related Receptor Tyrosine Kinase 3 (FLT-3) epidermal growth factor (EGFR), Mitogen-activated protein kinase (MEK), phosphatidylinositol-3-kinase (PI3K) and other protein kinase inhibitors, histone lysine specific demethylase 1 (LSD1) inhibitors, and WNT pathway inhibitors, alkylating agents and DNA repair pathway inhibitors, anti-hormonal agents, anti-cancer antibodies, and other cytotoxic chemotherapy agents.

In another embodiment, the invention provides a method of treating and/or preventing a fibrotic disease in a mammal in need thereof comprising administering to said mammal an effective amount of the formulations of the invention.

In a preferred embodiment, the fibrotic disease is selected from the group consisting of pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, and reactive fibrosis.

In one embodiment, the method of treating and/or preventing a fibrotic disease in a mammal in need thereof can include administering an additional anti-fibrotic agent.

DETAILED DESCRIPTION OF THE INVENTION

Definitions

Figure 1:
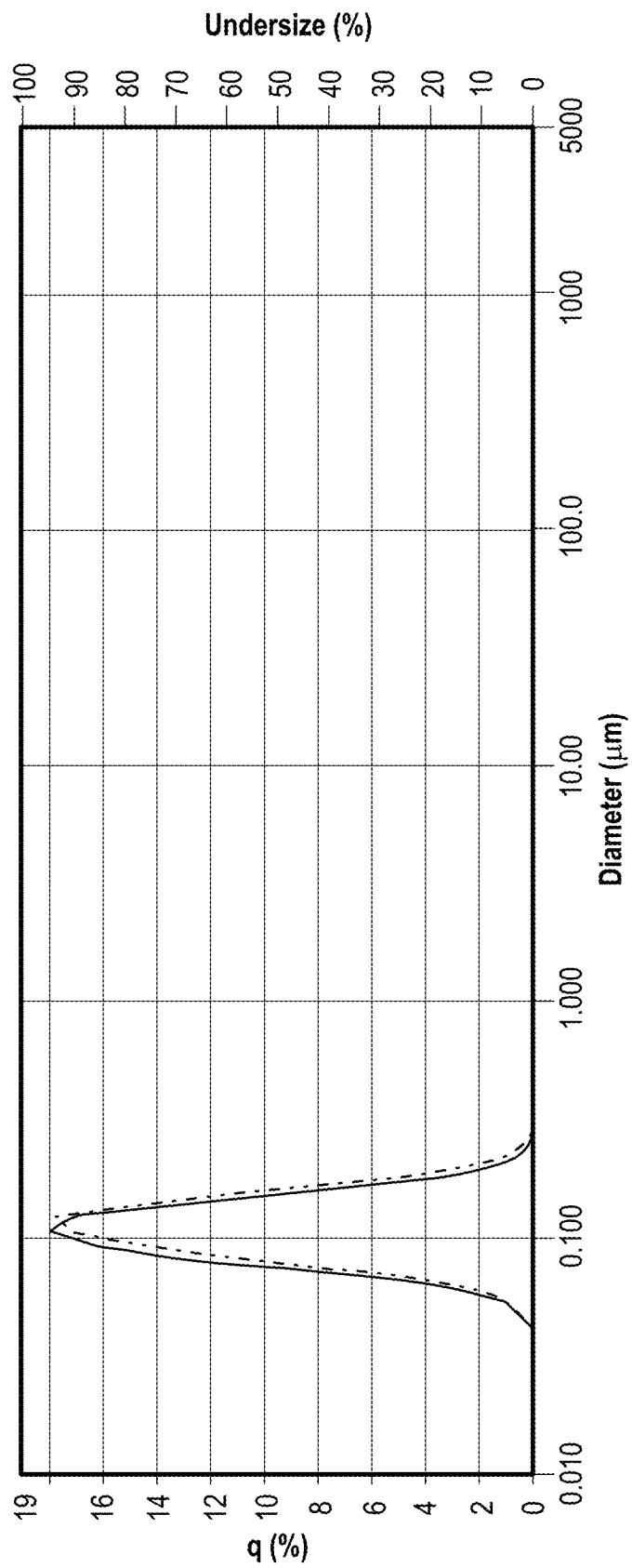
FIG. 1 is a Particle Size Distribution (PSD) overlay of one of the inventive formulations.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to the various embodiments given in this specification.

Unless otherwise defined, all technical and scientific terms used herein have the same meaning as commonly understood by one of ordinary skill in the art to which this invention pertains. In the case of conflict, the present document, including definitions will control.

The term "tegavivint" refers to a compound having the following structure:

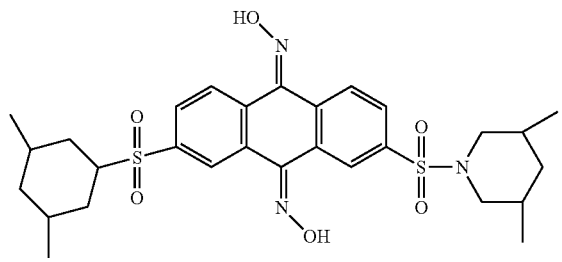

The term "BC2059" is used interchangeably with "tegavivint."

The term "long-term storage" or "long-term stability" is understood to mean that the pharmaceutical composition can be stored for three months or more, for six months or more, twelve months or more, and eighteen months or more. Long term storage is also understood to mean that the pharmaceutical composition is stored at 2-8° C. or at room temperature 15-25° C., or at any temperature between 2-8° C. and 15-25° C.

The term "stable" or "stabilized" with respect to long-term storage is understood to mean that active ingredient contained in the pharmaceutical compositions does not lose more than 20%, or more preferably 15%, or even more preferably 10%, and most preferably 5% of its activity relative to activity of the composition at the beginning of storage. Furthermore, for the purposes of this invention, the long-term physical stability of lyophilized formulation includes maintenance of good cake integrity, ability to readily re-suspend upon reconstitution with the respective diluent, and the absence of any significant crystal growth upon storage that can be determined by optical microscopy.

The term "mammal" includes, but is not limited to, a human.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "treatment" refers to any administration or application of remedies for disease in a mammal and includes inhibiting the disease, arresting its development, relieving the disease (for example, by causing regression, or restoring or repairing a lost, missing, or defective function) or stimulating an inefficient process. The term includes obtaining a desired pharmacologic and/or physiologic effect and covering any treatment of a pathological condition or disorder in a mammal. The effect may be prophylactic in terms of completely or partially preventing a disorder or symptom thereof and/or may be therapeutic in terms of a partial or complete cure for a disorder and/or adverse effect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "therapeutically effective amount" refers to an amount which, when administered to a living subject, achieves a desired effect on the living subject. For example, an effective amount of the compositions of the invention for administration to the living subject is an amount that prevents and/or treats any of the diseases mediated via the Wnt/β-catenin pathway. The exact amount will depend on the purpose of the treatment and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

The term "composition" or "formulation" refers to a mixture that usually contains a carrier, such as a pharmaceutically acceptable carrier or excipient that is conventional in the art and which is suitable for administration into a subject for therapeutic, diagnostic, or prophylactic purposes. For example, compositions for oral administration can form solutions, suspensions, tablets, pills, capsules, sustained release formulations, oral rinses or powders. The terms "composition," "pharmaceutical composition" and "formulation" are used interchangeably.

The term "nanoparticulate composition" refers to compositions wherein all, or almost all of the particles are less than 1000 nm.

The term "lyophilized formulation" refers to a formulation resulted from freeze-drying of an aqueous solution.

The term "pre-lyophilized formulation" refers to a formulation of the invention before any lyophilization takes place. The term encompasses formulations that will not undergo any lyophilization at all.

The term a "reconstituted formulation" refers to a formulation resulted from adding water (for example, sterile water) or an aqueous solvent to a solid composition in an amount to dissolve the composition. In one embodiment, the solid composition is a lyophilized formulation.

The term an "injectable formulation" refers to a formulation that is suitable for parenteral administration, e.g., subcutaneous, intravenous, intramuscular, or intraperitoneal administration.

The term "stable for therapeutic utility" refers to a tegavivint formulation that over a period of at least 6 months and preferably at least 18 months remains suitable for treatment of conditions treatable with tegavivint.

The term, "$AUC_{last}$," as used herein, refers to the last measurable drug concentration.

The term, "$C_{max}$," as used herein, refers to the maximum concentration that a drug achieves in a specified tissue after the drug has been administered and before the administration of a second dose.

The term, "$T_{max}$," as used herein, refers to the time after administration of a drug when the maximum plasma concentration is reached.

Formulations of the Invention

The inventors have unexpectedly and surprisingly discovered that a stable formulation can be made when it is produced utilizing Form I or Form IV polymorphs of tegavivint as starting material, when the starting material is subjected to high energy agitator milling at an elevated temperature of at least 40° C.-60° C., and preferably at about 60° C. Form I and Form IV polymorphs are described in detail in U.S. patent application Ser. No. 17/037,287, the contents of which are hereby incorporated by reference in their entirety.

In one embodiment, the invention provides a nanosuspension of tegavivint wherein the nanosuspension was prepared by a process comprising using either Form I or Form IV as the starting material and high energy agitator milling performed at a temperature of between about 40° C. and about 60° C., most preferably at about 60° C.

In one embodiment, the stable formulation can be produced starting with any of the polymorph forms of tegavivint (e.g., any of Form I, Form II, Form III or Form IV), as long as at some point within the production process, Form I and/or Form IV polymorphs are produced.

In one embodiment, if the milling process is done at temperature of less than about 60° C., the nanosuspension further undergoes the annealing process at or above 60° C.

Both polymorphic forms, Form I and Form IV, were utilized as starting materials for the controlled temperature high energy milling process. The milling used the concentration of tegavivint of 200 mg/ml and concentration of the stabilizer of 5% Poloxamer 188. Microscopic imaging and Differential Scanning Calorimeter (DSC) post milling analysis found that batches utilizing Form I as the starting material contained only Form I at the end product of the milling process. In contrast, the conversion of Form IV to Form I was seen in batches that utilized Form IV as the starting material. The milling of Form I at 60° C. or higher was hypothesized to prevent formation crystal seeds for the undesirable Form IV and result in a highly crystalline milled Form I material that is annealed and free of high energy particles and free of amorphous material. This finding was confirmed by the invention.

The end product obtained from milling at 60° C. using either Form I or Form IV as starting material was a nanosuspension of Form I, since Form IV was converted to Form I during milling over 120 min.

Consequently, in one embodiment, the invention allows to utilize either Form I or Form IV as the starting material for milling at an elevated temperature (40-60° C., preferably 60° C.) to obtain the final desired form (Form I). However, the advantage of using Form IV as a starting material for milling at 60° C. is that the system undergoes a full solvent mediated recrystallization from Form IV to Form i. The crystals for Form I grow "bottom-up" as they are milled, so the chance of getting any un-milled larger crystals is significantly diminished, thereby enhancing the quality of the suspension.

Indeed, the nanosuspension from milling Form IV at 60° C. was found to be a uniform, well-dispersed Form I with a narrow unimodal particulate size distribution. Upon stability analysis at 5° C. and ambient laboratory conditions), there were no significant change in particle size distribution. The microscopic images confirmed absence of any crystal growth for all final Form I formulations at the end of 3 months of storage.

In one embodiment, the milling is performed at a temperature of between about 40° C. and about 60° C., most preferably at about 60° C. Preferably, if the milling process is done at temperature of less than about 60° C., the nanosuspension further undergoes the annealing process at or above 60° C.

Nanosuspensions from the batch that utilized Form I as the starting material with Poloxamer 188 as the dispersant milled at elevated temperatures (60° C.) was then taken forward for the formulation optimization. Additionally, four batches, prepared at the original test scale, were milled and composited to provide the material for the formulation optimization study.

In one embodiment, the formulations of the invention, including but not limited to pre-lyophilized formulations, are filtered to remove any large particles. In one embodiment, the filter is 10 micron.

In one embodiment, the invention provides a formulation comprising particles of Form I or Form IV polymorph of tegavivint or a pharmaceutically acceptable salt, ester, amide, stereoisomer or geometric isomer thereof; wherein the particles have an effective D90 of less than or equal to 0.2 micron when measured using laser diffraction, and wherein the formulation was prepared by high energy agitator milling at a temperature of between about 40° C. and about 60° C.

In one embodiment, the formulation may be lyophilized.

In one embodiment, the particles have an effective D90 of less than or equal to 0.2 micron when measured using laser diffraction.

In one embodiment, the particles have an effective D50 of less than or equal to 0.12 micron when measured using laser diffraction.

In one embodiment, the particles have an effective D10 of less than or equal to 0.1 micron when measured using laser diffraction.

In some embodiments, the effective average particle size of tegavivint is about 4900 nm, about 4800 nm, about 4700 nm, about 4600 nm, about 4500 nm, about 4400 nm, about 4300 mm, about 4200 nm, about 4100 nm, about 4 microns, about 3900 nm, about 3800 nm, about 3700 nm, about 3600 nm, about 3500 nm, about 3400 mm, about 3300 nm, about 3200 nm, about 3100 nm, about 3 microns, about 2900 mm, about 2800 nm, about 2700 nm, about 2600 nm, about 2500 nm, about 2400 nm, about 2300 nm, about 2200 nm, about 2100 nm, about 2000 nm, about 1900 nm, about 1800 nm, about 1700 nm, about 1600 nm, about 1500 nm, about 1400 nm, about 1300 nm, about 1200 nm, about 1100 nm, about 1000 nm, about 900 nm, about 800 nm, about 700 nm, about 600 nm, about 500 nm, about 400 nm, or about 300 nm.

Further, in some embodiments, the effective average particle size of the compounds is less than 900 nm, more preferably less than 500 nm, and even more preferably, less than 300 nm.

The provided formulations are stable for therapeutic utility.

In one embodiment, the lyophilized formulations of the invention are anhydrous.

In one embodiment, the formulations, including lyophilized formulations, of the invention are stored in a dry atmosphere.

The storage temperature for the formulations of the invention can be about −20° C., about 5° C., or about 25° C.

In one embodiment, the invention provides a stable formulation comprising particles of tegavivint; wherein the particles have an effective D50 of less than or equal to 500 nm and D90 of less than or equal to 1.0 micrometer (μm) when measured using laser diffraction, wherein the formulation comprises tegavivint, a poloxamer, and one or more stabilizer selected from the group consisting of sucrose, trehalose and sorbitol, and wherein the formulation is prepared by high energy agitator milling at a temperature of between about 40° C. and about 60° C.

In one embodiment, tegavivint concentration in a formulation is 2% (20 mg/mL).

In one embodiment, tegavivint concentration in a formulation is 2.5% (25 mg/mL).

In another embodiment, tegavivint concentration in a formulation is 5% (50 mg/mL).

In one embodiment, the poloxamer is Poloxamer 188.

In one embodiment, the poloxamer concentration in a formulation is 6 mg/mL.

In another embodiment, the poloxamer concentration in a formulation is 12.5 mg/mL.

In one embodiment, the sucrose concentration in a formulation is 100 mg/mL.

In another embodiment, the trehalose concentration in a formulation is 100 mg/mL.

In one embodiment, the sorbitol concentration in a formulation is 50 mg/mL.

In one embodiment, the invention provides a stable lyophilized formulation comprising particles of tegavivint; wherein the particles have an effective D50 of less than or equal to 500 nm and D90 of less than or equal to 1.0 micrometer (μm) when measured using laser diffraction, wherein the formulation is a product of lyophilization of a pre-lyophilized formulation comprising tegavivint, a poloxamer, and one or more stabilizer selected from the group consisting of sucrose, trehalose and sorbitol.

In one embodiment, tegavivint concentration in a pre-lyophilized formulation is 2% (20 mg/mL).

In one embodiment, tegavivint concentration in a pre-lyophilized formulation is 2.5% (25 mg/mL).

In another embodiment, tegavivint concentration in a pre-lyophilized formulation is 5% (50 mg/mL).

In one embodiment, the poloxamer is Poloxamer 188.

In one embodiment, the poloxamer concentration in a pre-lyophilized formulation is 0.6%.

In another embodiment, the poloxamer concentration in a pre-lyophilized formulation is 1.25%.

In one embodiment, the sucrose concentration in a pre-lyophilized formulation is 10%.

In another embodiment, the trehalose concentration in a pre-lyophilized formulation is 10%.

In one embodiment, the sorbitol concentration in a pre-lyophilized formulation is 5%.

In one embodiment, the formulation is autoclaved prior to lyophilization.

In one embodiment, the lyophilization process comprises freezing the formulation to about −40° C., a primary drying step at −30° C. and a secondary drying step at about −10° C.

The invention also includes pre-lyophilized formulations of tegavivint.

In one embodiment, the pre-lyophilized formulation is prepared by a process comprising ball milling at a temperature of about 60° C.

In one embodiment, the pre-lyophilized formulation is prepared by a process comprising high energy milling at a temperature of about 60° C.

In one embodiment, the tegavivint in the pre-lyophilized formulation is Form I polymorph.

In one embodiment, the formulations of the invention are stable for three months, six months, twelve months or eighteen months at storage at a temperature of between 5° C. and 25° C.

In a preferred embodiment, the formulations of the invention exhibit long term stability.

In one embodiment, the formulations of the invention, including but not limited to lyophilized formulations of the invention, when reconstituted, may be formulated: (a) into a dosage form selected from the group consisting of tablets, and capsules; (b) into a dosage form selected from the group consisting of controlled release formulations, fast melt formulations, delayed release formulations, extended release formulations, pulsatile release formulations, and mixed immediate release and controlled release formulations; (c) into a dosage form suitable for inhalation or parenteral administration, including intramuscular, subcutaneous, intravenous and intradermal injection; (d) any combination of (a), (b) and (c).

In one embodiment, the formulations of the invention, including but not limited to the lyophilized formulations of the invention, when administered to rats via intravenous (IV) infusion at 15.5 mg/mL concentration, result in one or more of the following values: $C_{max}$ of at least about 50,000 ng/mL in plasma; at least about 200 ng/g in brain; at least about 2900 ng/g in heart; at least about 3700 ng/g in kidney; at least about 35000 ng/g in lungs; at least about 400 ng/g in pectoral thigh muscle; at least about 360000 ng/g in spleen; at least about 470 ng/g in visceral fat; and at least about 237,000 ng/g in liver. In another embodiment, the formulations of the invention, including but not limited to the lyophilized formulations of the invention, when administered to rats via IV infusion at 15.5 mg/mL concentration, result in one or more of the following values: $AUC_{last}$ of at least about 68,000 hr·ng/mL in plasma; at least about 1800 hr·ng/g in brain; at least about 45000 hr·ng/g in heart; at least about 58000 hr·ng/g in kidney; at least about 450000 hr·ng/g in lungs; at least about 5700 hr·ng/g in pectoral thigh muscle; at least about 4800000 hr·ng/g in spleen; at least about 4000 hr·ng/g in visceral fat; and at least about 3,600,000 hr·ng/g in liver.

In another embodiment, the formulations of the invention, including but not limited to the lyophilized formulations of the invention, when administered to rats via IV infusion at 15.5 mg/mL concentration, result in one or more of the following values: $T_{max}$ of about 0.08 hr or less in plasma; about 0.5 hr or less in brain; about 1 hr or less in heart; about 0.5 hr or less in kidney; about 0.5 hr or less in lungs; about 0.5 hr or less in pectoral thigh muscle; about 0.5 hr or less in spleen; about 1 hr or less in visceral fat; and about 1 hr or less in liver.

The pharmaceutical formulations of the invention can further comprise one or more pharmaceutically acceptable excipients, carriers, or a combination thereof.

In another embodiment, the invention provides a method of preventing, treating or ameliorating cancer or tumor metastasis in a mammal in need thereof comprising administering to said mammal an effective amount of the formulations of the invention.

The method of administering is not limited to any specific route of administration, and includes, but is not limited to, intravenous, parenteral, oral, inhalation (including aerosolized delivery), buccal, intranasal, rectal, intra-lesional intraperitoneal, intradermal, transdermal, subcutaneous, intra-arterial, intracardiac, intraventricular, intracranial, intratracheal, intrathecal administration, intramuscular injection, intravitreous injection, and topical application methods.

In another embodiment, the method of preventing, treating or ameliorating cancer or tumor metastasis in a mammal in need thereof can include administering an additional anti-cancer agent and/or cancer therapy (for example, cancer vaccines, anti-cancer adoptive cell therapies and radio therapies).

In one embodiment, the additional anti-cancer agent is selected from the group consisting of antimitotic agents, antimetabolite agents, histone deacetylase (HDAC) inhibitors, proteosome inhibitors, immunotherapeutic agents, Fms Related Receptor Tyrosine Kinase 3 (FLT-3) epidermal growth factor (EGFR), Mitogen-activated protein kinase (MEK), phosphadtidylinositol3kinase (PI3K) and other protein kinase inhibitors, histone lysine specific demethylase 1 (LSD1) inhibitors, and WNT pathway inhibitors, alkylating agents and DNA repair pathway inhibitors, anti-hormonal agents, anti-cancer antibodies, and other cytotoxic chemotherapy agents.

In another embodiment, the invention provides a method of treating and/or preventing a fibrotic disease in a mammal in need thereof comprising administering to said mammal an effective amount of the formulations of the invention.

In a preferred embodiment, the fibrotic disease is selected from the group consisting of pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, and reactive fibrosis.

In one embodiment, the method of treating and/or preventing a fibrotic disease in a mammal in need thereof can include administering an additional anti-fibrotic agent.

The invention encompasses formulations including tegavivint and a pharmaceutically acceptable salt, ester, amide, stereoisomer or geometric isomer thereof.

In one embodiment, the compositions of the invention, when reconstituted, may be formulated: (a) into a dosage form selected from the group consisting of tablets, and capsules; (b) into a dosage form selected from the group consisting of controlled release formulations, fast melt formulations, delayed release formulations, extended release formulations, pulsatile release formulations, and mixed immediate release and controlled release formulations; (c) into a dosage form suitable for inhalation or parenteral administration, including intramuscular, subcutaneous, intravenous and intradermal injection; (d) any combination of (a), (b) and (c).

The compositions of the invention can further comprise one or more pharmaceutically acceptable excipients, carriers, or a combination thereof.

The pharmaceutically acceptable excipients used in the formulation of the present invention can act in more than one way.

The pharmaceutically acceptable excipients can be, for example, a dispersion medium, a dispersion emulsifier, a dispersion enhancer, or a combination thereof.

Examples of the propellant include, but not limited to, HFA-134a (1, 1,1,2-tetrafluoroethane), HFA-227 (1,1,1,2,3,3,3-heptafluoropropane), a combination thereof, etc.

The dispersion medium can be, for example, ethanol, propylene glycol, polyethylene glycol 200, polyethylene glycol 300, polyethylene glycol 400, glycerin, a combination thereof, etc.

The dispersion emulsifier (enhancer) can be, for example, $H_2O$, oleic acid, sodium lauryl sulfate, polyethylene glycol 1000, ammonium alginate, potassium alginate, calcium stearate, glyceryl monooleate, polyoxyethylene stearates, emulsifying wax, polysorbate 20, polysorbate 40, polysorbate 60, polysorbate 80, sorbitan monolaurate, sorbitan monooleate, sorbitan monopalmitate, sorbitan monostearate, sorbitan sesquioleate, sorbitan trioleate, poloxamer, a combination thereof, etc.

Examples of the dispersion enhancers include, but not limited to, polysorbate 20, polysorbate 40, polysorbate 60, polysorbate 80, carboxymethylcellulose sodium, hypromellose, ethylene glycol stearates, sorbitan monolaurate, sorbitan monooleate, sorbitan monopalmitate, sorbitan monostearate, sorbitan sesquioleate, sorbitan trioleate, glyceryl monostearate, lecithin, meglumine, poloxamer, polyoxyethylene alkyl ethers, polyoxyl 35 castor oil, polyoxyethylene stearates, polyoxylglycerides, pyrrolidone, sorbitan esters, stearic acid, vitamin E polyethylene glycol succinate, polyethylene glycol 1000, povidone, a combination thereof, etc.

The compositions of the invention can be suitable for all routes of administration, including but not limited to, intravenous, parenteral, oral, inhalation (including aerosolized delivery), buccal, intranasal, rectal, intra-lesional intraperitoneal, intradermal, transdermal, subcutaneous, intra-arterial, intracardiac, intraventricular, intracranial, intratracheal, intrathecal administration, intramuscular injection, intravitreous injection, and topical application methods.

Pharmaceutical compositions according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Examples of filling agents are lactose monohydrate, lactose anhydrous, and various starches; examples of binding agents are various celluloses and cross-linked polyvinylpyrrolidone, microcrystalline cellulose, such as cellulose powder sold under the trademarks Avicel® PH101 and Avicel® PH102, microcrystalline cellulose, and silicified microcrystalline cellulose (ProSolv SMCC™) Suitable lubricants, including agents that act on the flowability of the powder to be compressed, are colloidal silicon dioxide, such as Aerosil® 200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like.

Examples of preservatives are potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quarternary compounds such as benzalkonium chloride.

Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as anhydrous lactose sold under the trademark Avicel® PH101 and Avicel® PH102; lactose such as lactose monohydrate, lactose anhydrous, and anhydrous lactose sold under the trademark Pharmatose® DCL21; dibasic calcium phosphate such as calcium hydrogen phosphate dihydrate sold under the trademark Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts.

Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

Tegavivint has the following structure:

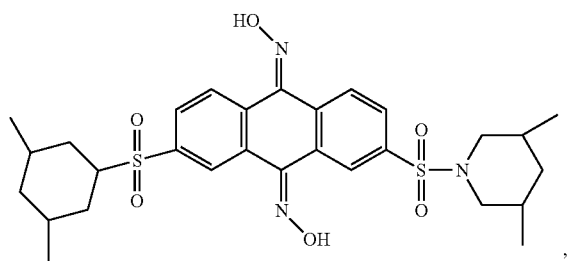

or a pharmaceutically acceptable salt, ester, amide, stereoisomer or geometric isomer thereof.

In another embodiment, the invention provides a method of preventing, treating or ameliorating cancer or tumor metastasis in a mammal in need thereof comprising administering to said mammal an effective amount of the compositions of the invention.

In another embodiment, the method of method of preventing, treating or ameliorating cancer or tumor metastasis in a mammal in need thereof can include administering an additional anti-cancer agent and/or cancer therapy (for example, cancer vaccines, anti-cancer adoptive cell therapies and radio therapies).

In one embodiment, the additional anti-cancer agent is selected from the group consisting of antimitotic agents, antimetabolite agents, histone deacetylase (HDAC) inhibitors, proteosome inhibitors, immunotherapeutic agents, Fms Related Receptor Tyrosine Kinase 3 (FLT-3) epidermal growth factor (EGFR), Mitogen-activated protein kinase (MEK), phosphadtidylinositol3kinase (PI3K) and other protein kinase inhibitors, histone lysine specific demethylase 1 (LSD1) inhibitors, and WNT pathway inhibitors, alkylating agents and DNA repair pathway inhibitors, anti-hormonal agents, anti-cancer antibodies, and other cytotoxic chemotherapy agents.

In another embodiment, the invention provides a method of treating and/or preventing a fibrotic disease in a mammal in need thereof comprising administering to said mammal an effective amount of the nanoparticulate compositions of the invention.

In a preferred embodiment, the fibrotic disease is selected from the group consisting of pulmonary fibrosis, Dupuytren's contracture, scleroderma, systemic sclerosis, scleroderma-like disorders, sine scleroderma, liver cirrhosis, interstitial pulmonary fibrosis, keloids, chronic kidney disease, chronic graft rejection, and other scarring/wound healing abnormalities, post-operative adhesions, reactive fibrosis.

The present invention is more particularly described in the following examples that are intended as illustrative only, since many modifications and variations therein will be apparent to those skilled in the art. In the following examples it should be understood that weight percentages of various ingredients are expressed as w/v percentages.

EXAMPLES OF THE INVENTION

It was very challenging and difficult to arrive at a stable formulation of tegavivint.

Example 1

Temperature-Controlled High Energy Milling

The objective of this experiment was to translate findings from thermal and crystallographic analysis of selected forms to perform temperature-controlled milling followed by formulation optimization including lyophilization. An additional objective was to confirm the short-term stability of nanosuspensions by evaluating potential crystal growth or formation of amorphous material during 18-month storage period. Temperature controlled milling was performed at a 5 mL scale using high energy milling.

Both polymorphic forms, Form I and Form IV, were utilized as starting materials for the controlled temperature high energy milling process.

Out of the four-test suspension milled, two of test suspensions were of interest and thus taken forward. The two lead test suspensions at 200 mg/mL API, outlined in Table 1 were processed using the milling parameters outlined in Table 2. For each preparation, the API and dispersant solution were added to the mill chamber and mixed to disperse. Milling media (0.5-mm polymeric spheres) was added to the suspension and allowed to settle before the chamber was attached to the mill and the material processed.

TABLE 1

Test Batch Comparison

| Test batch/preparations | 1 | 4 |
|---|---|---|
| Batch number | 191122_For_021 | 200106_For_012 |
| API form | Form I | Form IV |
| Dispersant | 5% poloxamer 188 | 5% poloxamer 188 |
| Temperature | 60° C. | 60° C. |

TABLE 2

High energy milling parameters

| | |
|---|---|
| Batch size | ~5 mL (90% of void mill volume) |
| Process type | Batch (non-recirculated) |
| Milling media | 0.5-mm (nominal) polymeric spheres |
| Media charge | 85% of chamber volume |
| Agitator | Solid, 28.8 mm diameter |
| Agitator speed | 2000 rpm (~3 m/s tip speed) |
| Extraction procedure | Centrifugal extraction with diluent rinsing |

The chamber was allowed to equilibrate to the designated temperature before agitation. Once the milling time had been achieved, the batches milled at elevated temperature were actively cooled to 25° C. before sampling. Centrifugal extraction was used to separate the completed suspensions from the milling media. For stability determinations, 0.5-mL aliquots of the suspensions were added volumetrically to 2-mL glass serum vials and sealed with a butyl stopper/aluminum crimp seal.

Particle-size distribution (PSD) measurements and optical microscopy were performed on the test suspensions. PSD measurements were made using the parameters listed in Table 3. Typically, microscopic evaluations were made at 400× magnification with bright-field illumination, though other visualizations were occasionally employed to highlight certain features of the suspensions. Un-milled API was similarly analyzed to provide a comparative baseline.

TABLE 3

Particle-Size Distribution Measurement Parameters

| | |
|---|---|
| Technique | Laser diffraction |
| Instrument | Horiba LA-960 |
| Refractive Index | 1.60 |
| i-value | 0.0 |
| Convergence (algorithm iterations) | 15 (default) |
| Dispersant | Deionized water |
| Distribution base | Volume |

Figure 2:
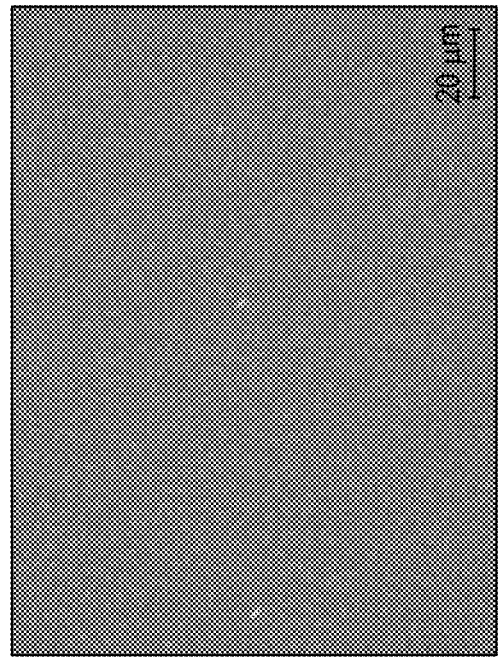
FIG. 2 is an optical microscopy image of the same inventive formulation shown in FIG. 1.
Figure 2:
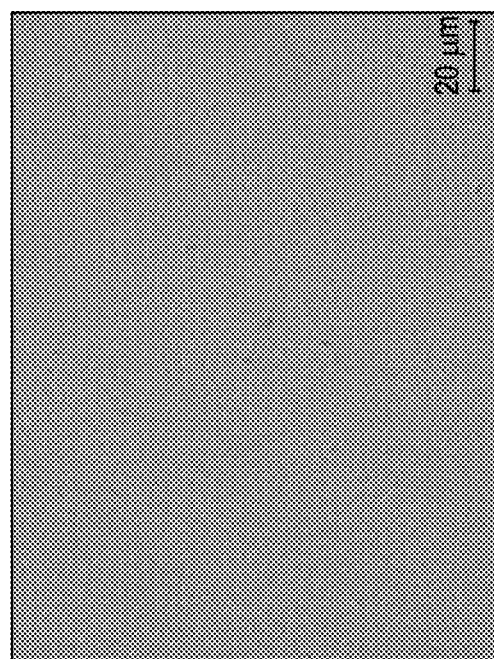

Preparation 1 (PSI batch 191122_For_021) was milled for 2 hours and resulted in a narrow monomodal PSD with a median size of 0.11 μm and D90 of 0.15 μm. An additional hour of milling did not produce a discernable size change, as shown in the PSD overlay in FIG. 1 (solid line is 120 min; dashed line is 180 min). Optical microscopy, in FIG. 2, shows a uniform, well-dispersed nanosuspension.

Microscopy images from Bright filed and Phase contrast (400×) of the milled material also confirmed uniform size and well-dispersed nanosuspension distributions after the high energy milling process at elevated temperature. The microscopic images confirmed absence of any un-milled material.

Figure 3:
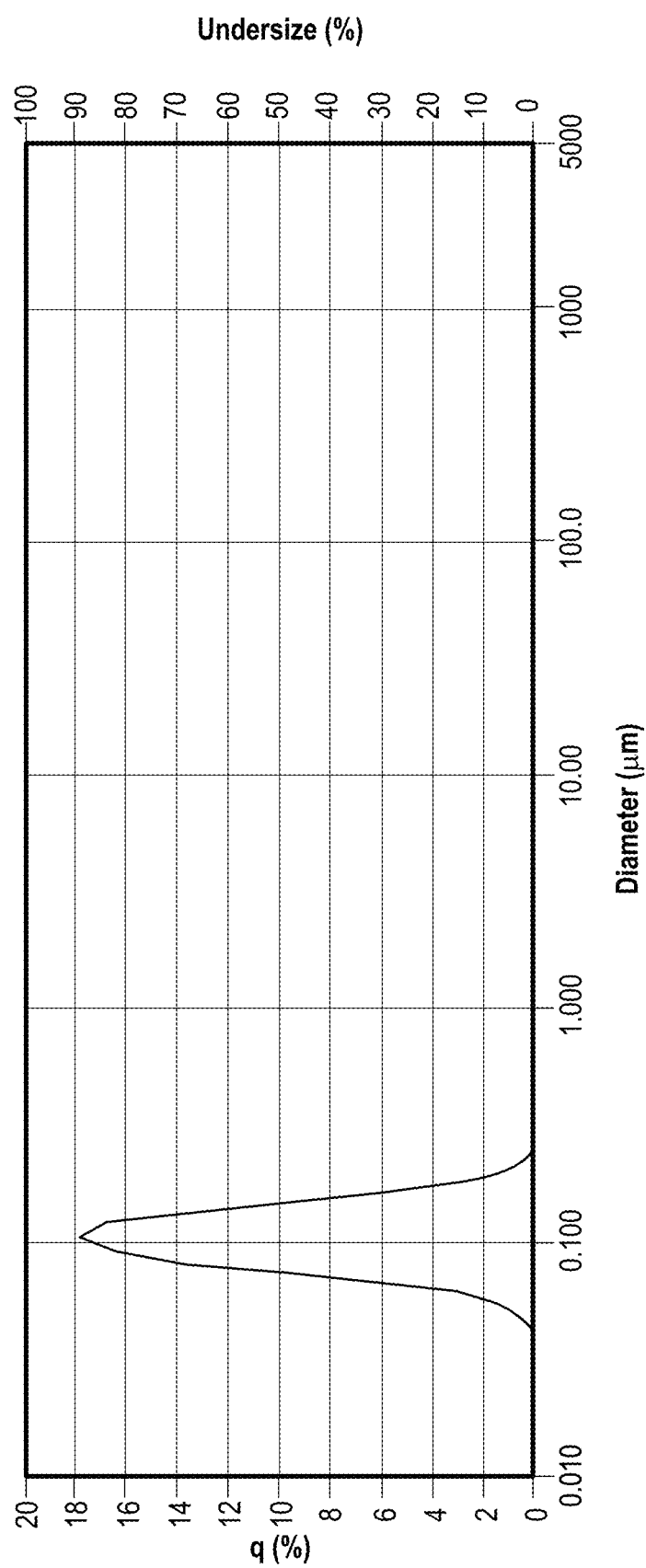
FIG. 3 is a PSD overlay of another inventive formulation.
Figure 4:
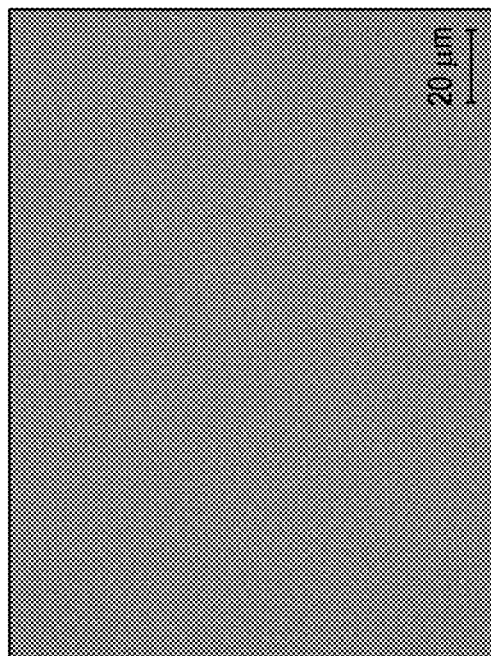
FIG. 4 is an optical microscopy image of the same inventive formulation shown in FIG. 3.

Preparation 4 (PSI batch 200106_For_012) was milled for 2 hours and resulted in a narrow monomodal PSD with a median size of 0.11 μm and D90 of 0.15 μm, shown in FIG. 3. Optical microscopy, in FIG. 4, shows a uniform, well-dispersed nanosuspension.

Likewise, microscopy images from Bright field and Phase contrast (400×) of the milled material also confirmed uniform size and well-dispersed nanosuspension distributions after the high energy milling process at elevated temperature. The microscopic images confirmed absence of any un-milled material.

Example 2

Thermal Analysis of Tegavivint Nanoparticles

Microscopic imaging and DSC post-milling found that batches utilizing Form I as the starting material contained only Form I at the end product of the milling process.

To determine if crystal-forms had been affected by high-temperature milling, Tegavivint nanoparticles derived from both crystal forms were separated from Preparations 1 and 4 (see, Example 1) by successive iterations of centrifugation, decanting, and resuspension with deionized water. The isolated solids were dried at ambient conditions over silica desiccant. DSC was performed on the dried nanoparticles, heating from 25° C. to 300° C. at 10 degrees per minute. Un-milled API was similarly analyzed for comparison.

Un-milled API forms I and IV correlated well with previous thermal data. The data for milled Form I correlated with the data from un-milled Form i. The nanoparticles collected from the milled Form IV did not exhibit the expected thermal event at 167° C., suggesting a conversion to Form I during high-temperature milling. The isolated particles also showed an additional endotherm at 52° C. that correlates with the melting point of poloxamer 188, suggesting residual excipient is associated with the isolated particles.

Example 3

Stability of Suspension Preparations 1 and 4 for Up to 3 Months

Procedure:

Several aliquots of the nanosuspensions (Form I) obtained from high energy milling of Preparation 1 and 4 at elevated temperature were placed at 5° C. and ambient laboratory conditions (~25° C.) to evaluate stability up to 3 months. The samples were pulled at specific time points for evaluation of particle size distribution and microscopy to determine if there were no significant change in particle size distribution and to the confirm absence of any crystal growth from the microscopy during storage. The equipment utilized for this assessment is listed below.

Equipment Utilized for PSD and Microscopy Assessments:
Particle-size analyzer: Horiba LA-960
Microscope: Leica DMRB and Olympus BX51

Figure 5:
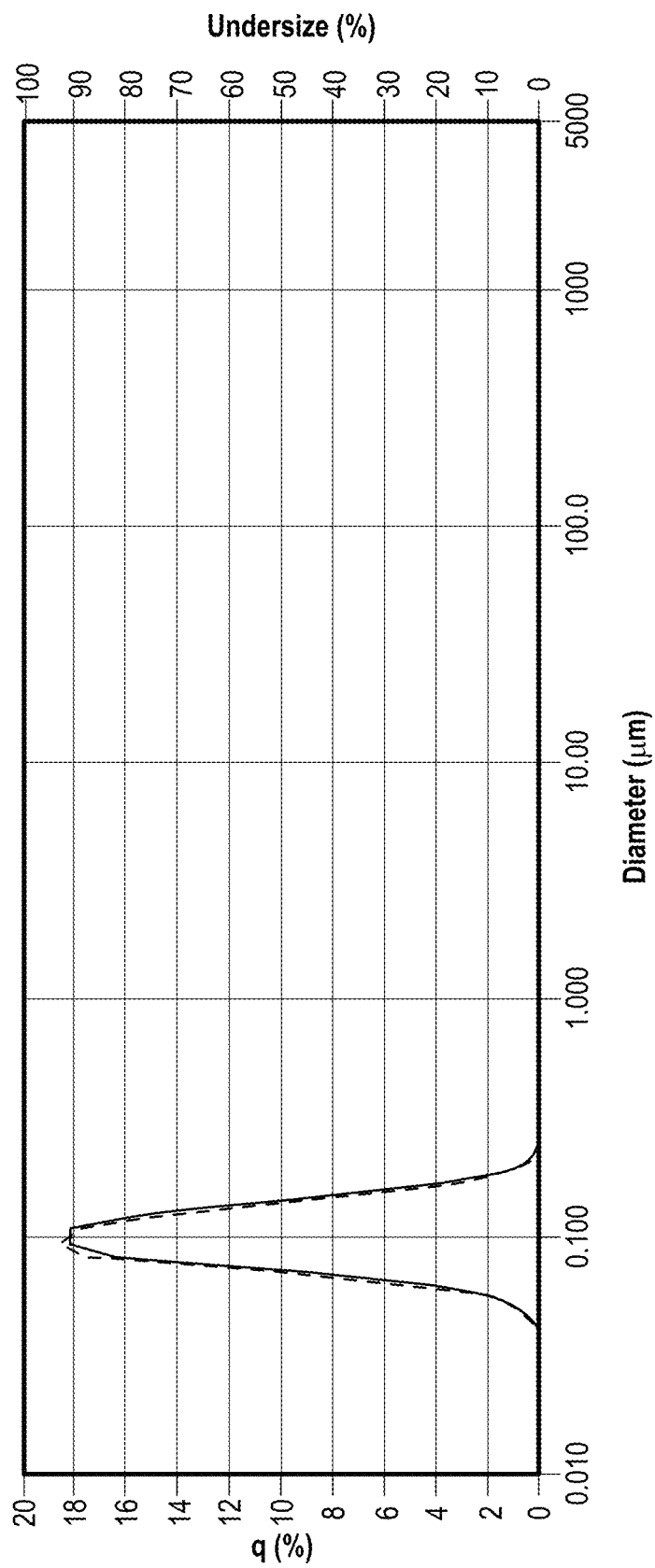
FIG. 5 is a PSD overlay of one of the inventive formulations at 1 month.
Figure 6:
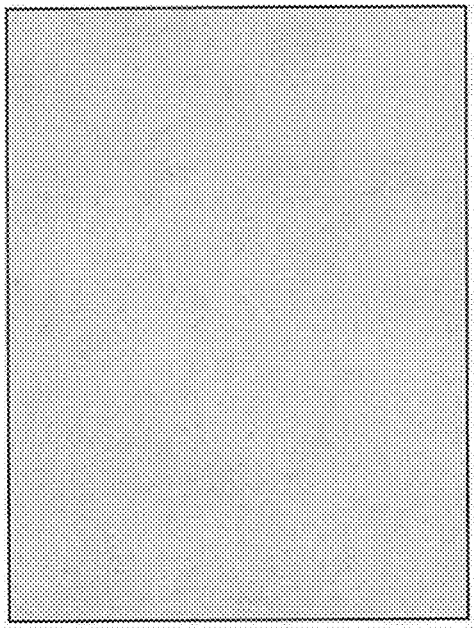
FIG. 6 is an optical microscopy image of the same inventive formulation shown in FIG. 5.
Figure 6:
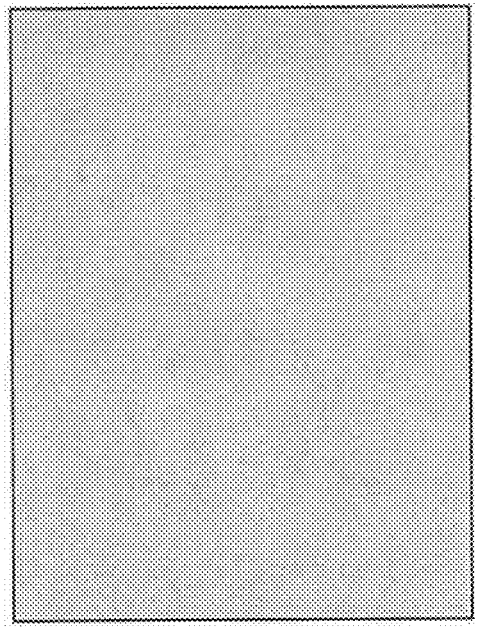

FIG. 5 demonstrates Particle Size Distribution of Preparation 1 at one month. FIG. 6 shows microscopy images of Preparation 1 at one month.

At the T=0 (Particle Size distribution from FIG. 1) the D10, Median and the D90 results were 0.07663 μm, 0.11239 μm and 0.16239 μm respectively. After 20 days of stability studies of nanosuspension Preparation 1 individually placed on stability at 5° C. and 25° C. showed no significant change in the particulate size distribution as indicated by the following results. The D10, Median and the D90 results from the 5° C. condition were 0.07063 μm, 0.10020 μm and 0.14353 μm. The D10, Median and the D90 results from the 25° C. condition were 0.06945 μm, 0.09773 μm and 0.14058 μm. The distribution from 5° C. and 25° C. shows an overlap indicating no significant changes when stored at 5° C. vs 25°

C. Solid curve corresponds to 5° C. condition and dashed curve corresponds to 25° C. condition.

Comparison of the images from Microscopy (Bright field and Phase contrast (400×)) at T=0 (FIG. 2) and at the end of 20 days (FIG. 6), showed no significant changes to the distributions. The suspensions continue to exhibit uniform size and are well-dispersed. The microscopic images confirmed absence of any crystal growth during storage.

Figure 7:
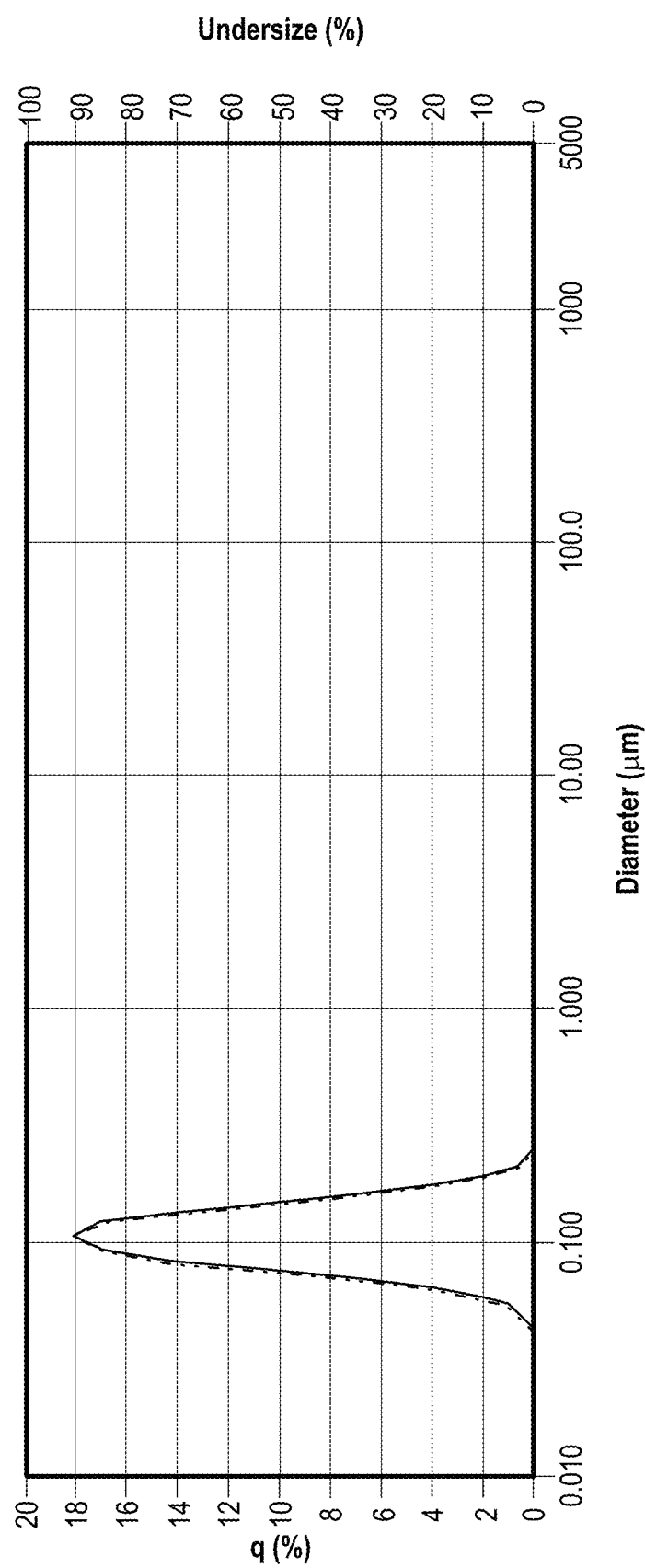
FIG. 7 is a PSD overlay of one of the inventive formulations at 3 months.

At the T=0 (Particle Size distribution from FIG. 1) the D10, Median and the D90 results were 0.07663 µm, 0.11239 µm and 0.16239 µm respectively. After 3 months of stability studies of the nanosuspension from Preparation 1 individually placed on stability at 5° C. and 25° C. showed no significant changes in the particulate size distribution as indicated by the following results. The D10, Median and the D90 results from the 5° C. condition were 0.07351 µm, 0.10600 µm and 0.15095 µm. The D10, Median and the D90 results from the 25° C. condition were 0.07251 µm, 0.10443 µm and 0.14918 µm. The distribution from 5° C. and 25° C. shows an overlap indicating no significant changes when stored at 5° C. vs 25° C. See, FIG. 7. Solid curve corresponds to 5° C. condition and dashed curve corresponds to 25° C. condition.

Figure 8:
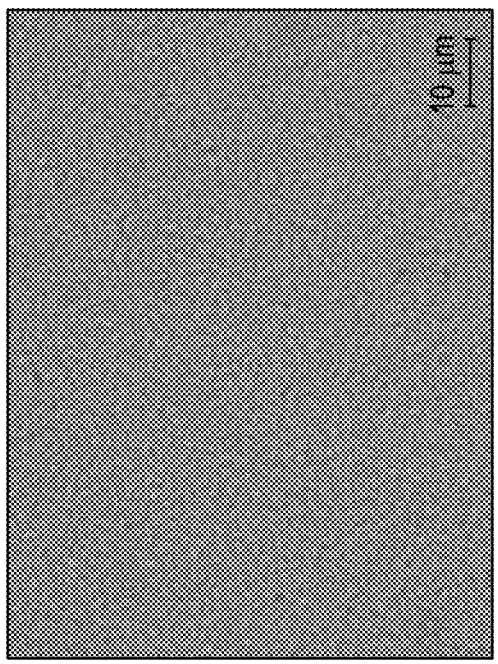
FIG. 8 is an optical microscopy image of the same inventive formulation shown in FIG. 7.
Figure 8:
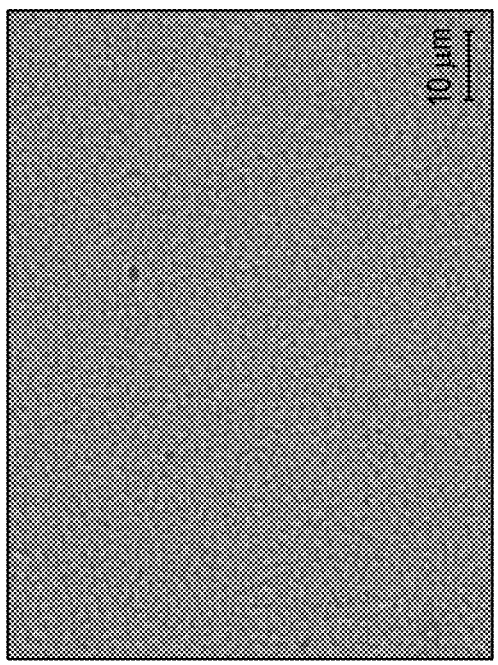

FIG. 8 shows 3-Month Microscopy of Preparation 1 (1000×, 5° C. and 25° C.)

Comparison of the images from Microscopy (Bright filed and Phase contrast (400×)) at T=0 (FIG. 2) and at the end of 3 Months showed no significant changes to the distributions. The suspensions continue to exhibit uniform size and are well-dispersed. The microscopic images confirmed absence of any crystal growth during storage.

Figure 9:
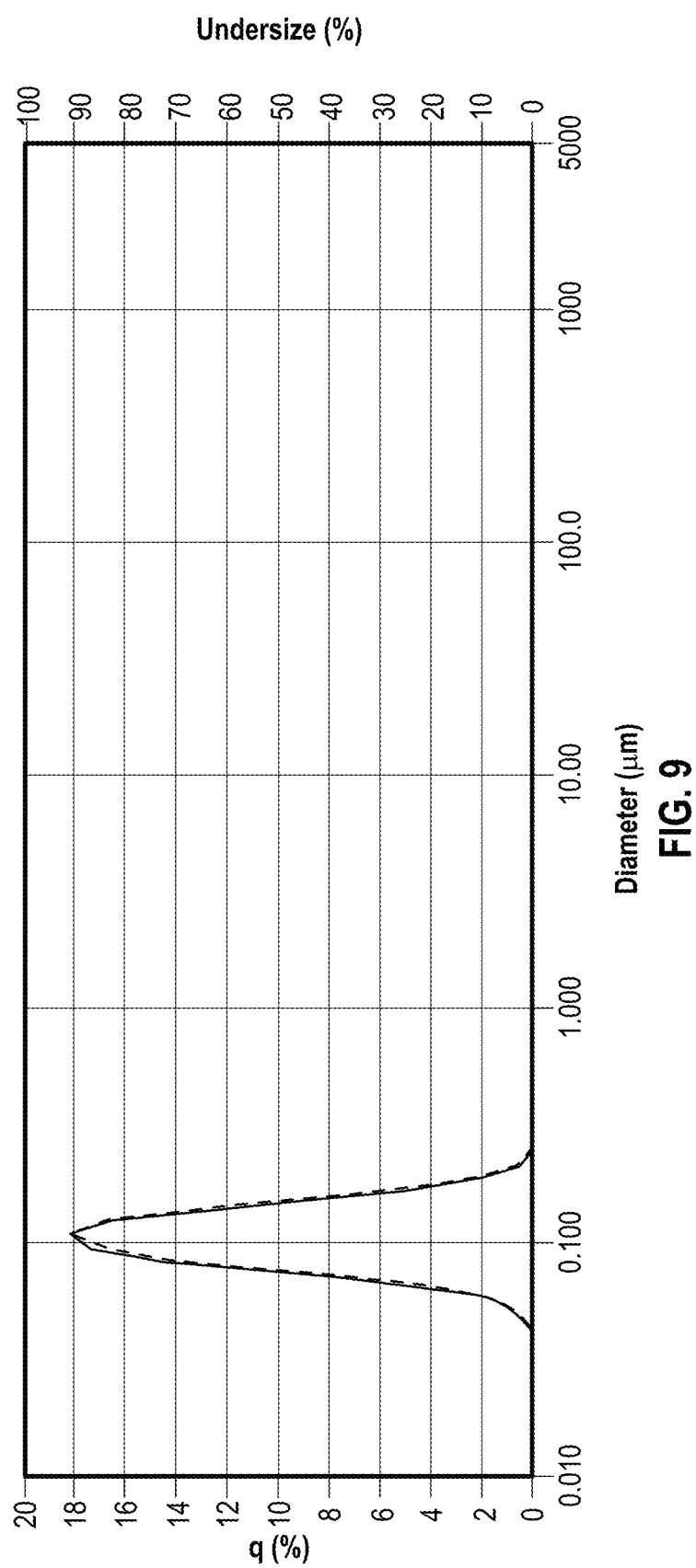
FIG. 9 is a PSD overlay of another inventive formulation at 4 days.

At the T=0 (Particle Size distribution from FIG. 3) the D10, Median and the D90 results were 0.07298 µm, 0.10578 µm and 0.15163 µm respectively. After 4 days of stability studies of nanosuspension from Preparation 4 individually placed on stability at 5° C. and 25° C. showed no significant change in the particulate size distribution as indicated by the following results. The D10, Median and the D90 results from the 5° C. condition were 0.07193 µm, 0.10321 µm and 0.14729 µm. The D10, Median and the D90 results from the 25° C. condition were 0.07288 µm, 0.10516 µm and 0.14967 µm. The distribution from 5° C. and 25° C. shows an overlap indicating no significant changes when stored at 5° C. vs 25° C. See, FIG. 9. Solid curve corresponds to 5° C. condition and dashed curve corresponds to 25° C. condition.

Figure 10:
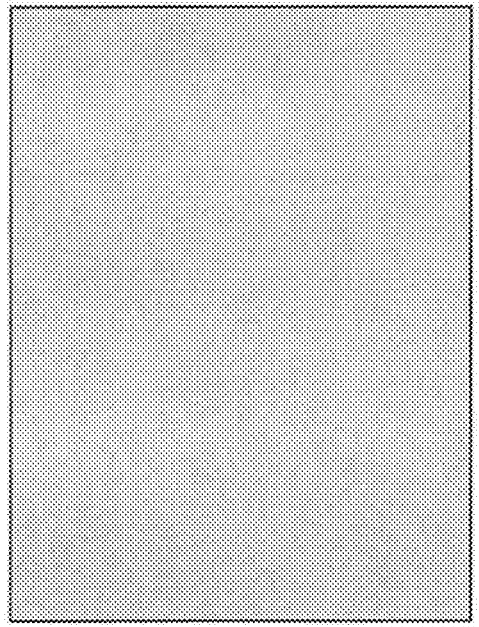
FIG. 10 is an optical microscopy image of the same inventive formulation shown in FIG. 9.
Figure 10:
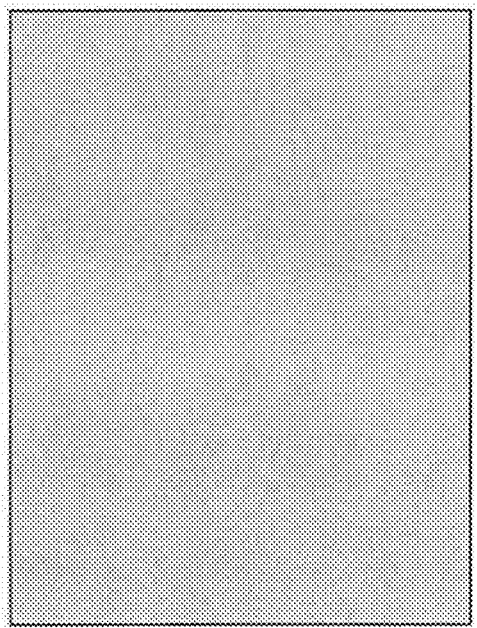

Comparison of the images from Microscopy (Bright field and Phase contrast (400×)) at T=0 (FIG. 4) and at the end of 4 days showed no significant changes to the distributions. The suspensions continue to exhibit uniform size and are well-dispersed. The microscopic images confirmed absence of any crystal growth during storage. See, FIG. 10.

Figure 11:
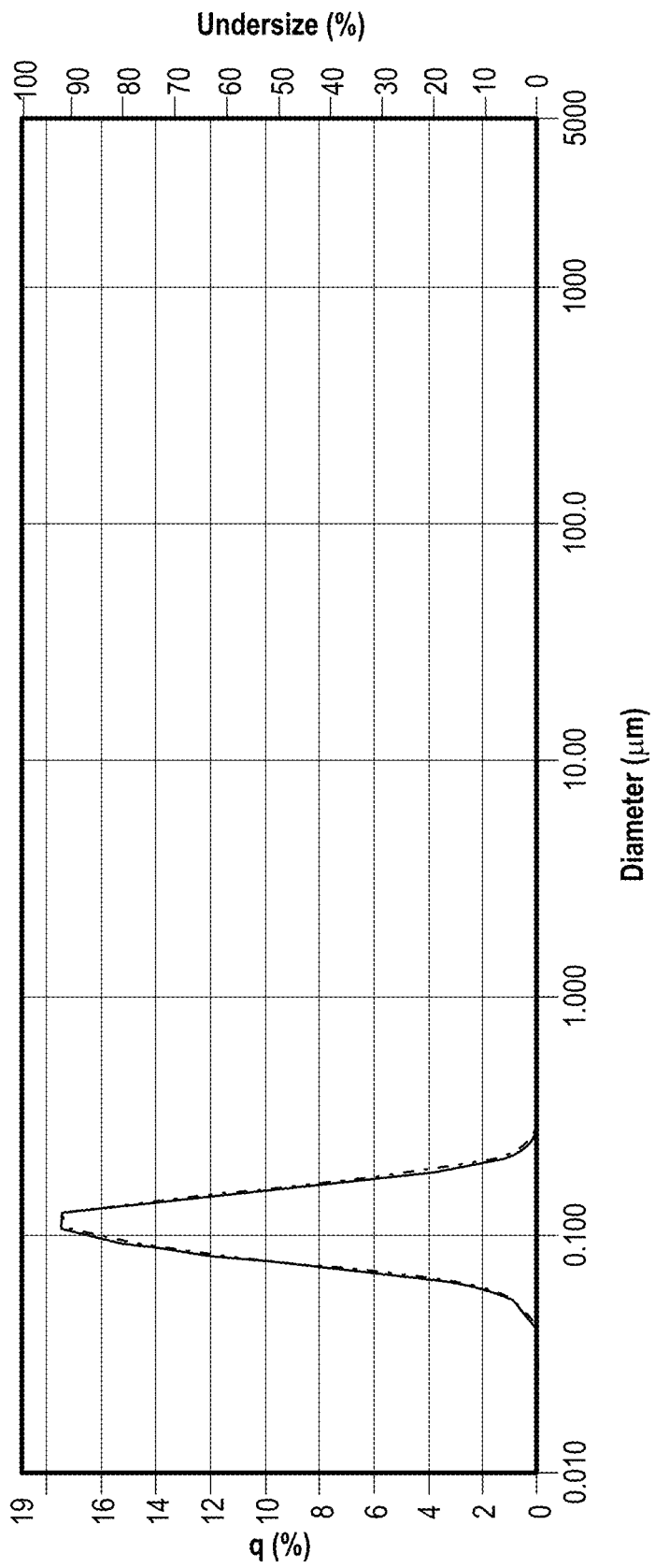
FIG. 11 is a PSD of one of the inventive formulations at 6 weeks.

FIG. 11 shows that at the T=0 (Particle Size distribution from FIG. 3) the D10, Median and the D90 results were 0.07298 µm, 0.10578 µm and 0.15163 µm respectively. After 6 weeks of stability studies of nanosuspension from Preparation 4 individually placed on stability at 5° C. and 25° C. showed no significant change in the particulate size distribution as indicated by the following results. The D10, Median and the D90 results from the 5° C. condition were 0.07521 µm, 0.10974 µm and 0.15883 µm. The D10, Median and the D90 results from the 25° C. condition were 0.07595 µm, 0.11113 µm and 0.16140 µm. The distribution from 5° C. and 25° C. shows an overlap indicating no significant changes when stored at 5° C. vs 25° C. Solid curve corresponds to 5° C. condition and dashed curve corresponds to 25° C. condition.

Figure 12:
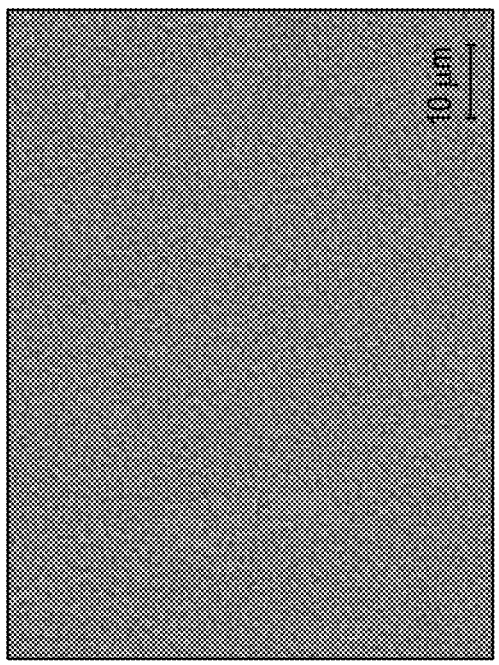
FIG. 12 is an optical microscopy image of the same inventive formulation shown in FIG. 11.
Figure 12:
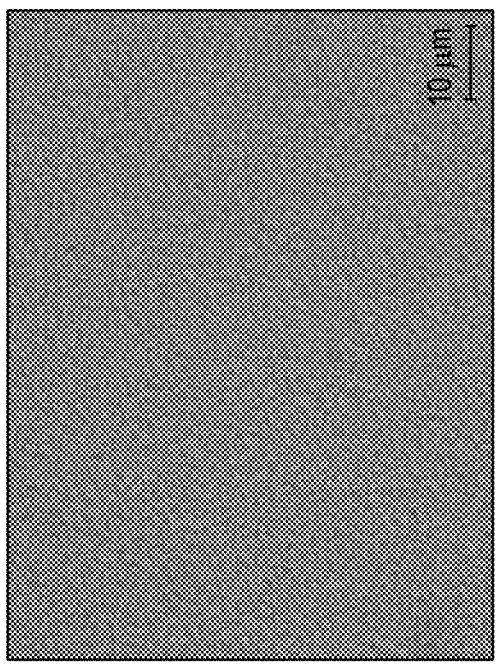

Comparison of the images from Microscopy (Bright field and Phase contrast (400×)) at T=0 (FIG. 4) and at the end of 6 weeks (FIG. 12) showed no significant changes to the distributions. The suspensions continue to exhibit uniform size and are well-dispersed. The microscopic images confirmed absence of any crystal growth.

Figure 13:
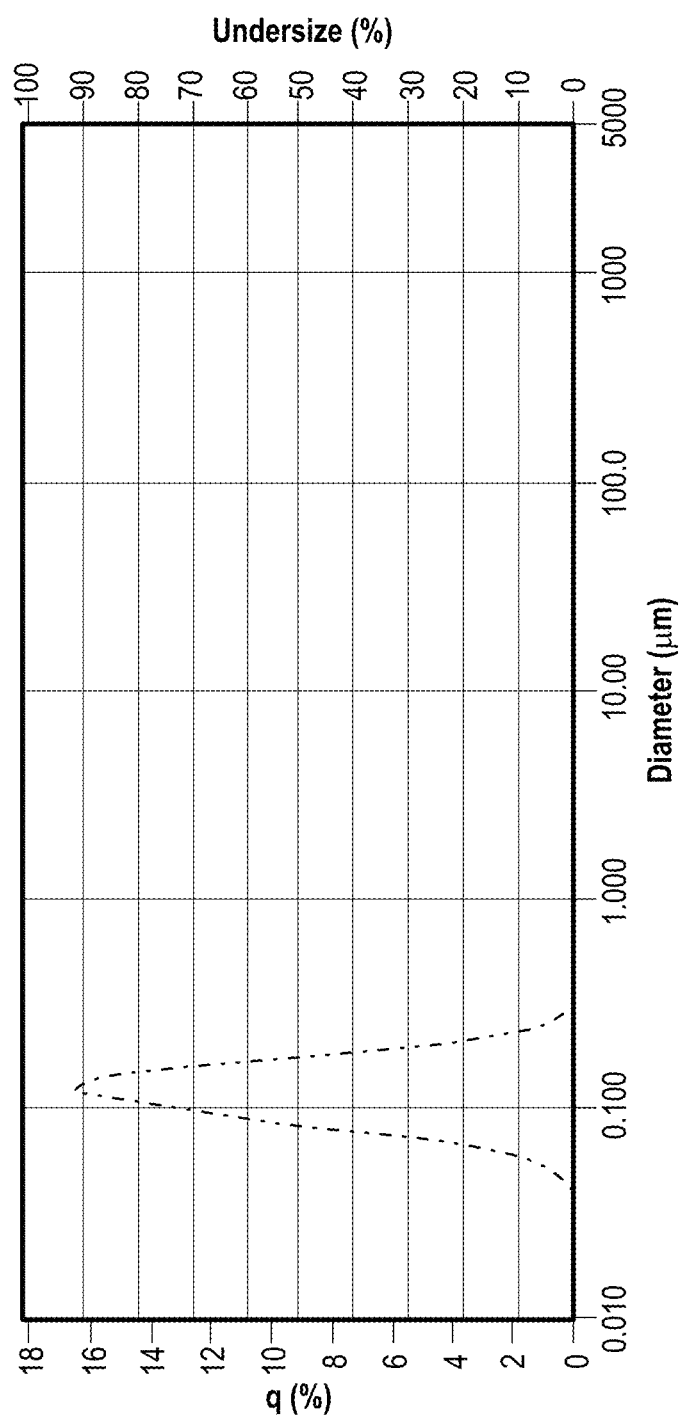
FIG. 13 is a PSD overlay of another inventive formulation before and after filtration.
Figure 14:
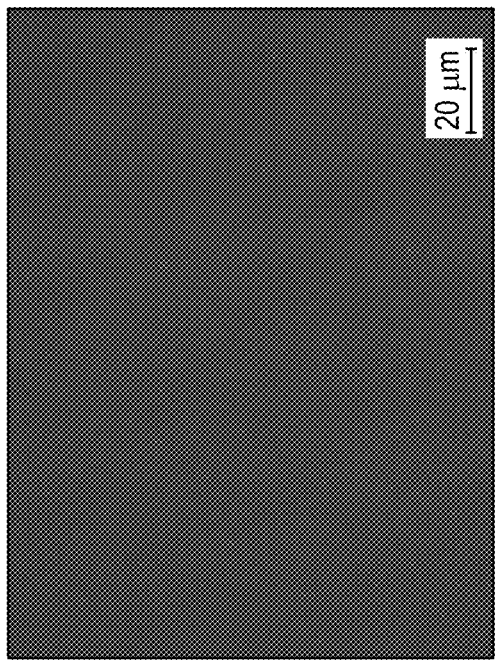
FIG. 14 is an optical microscopy image of the same inventive formulation shown in FIG. 13.
Figure 14:
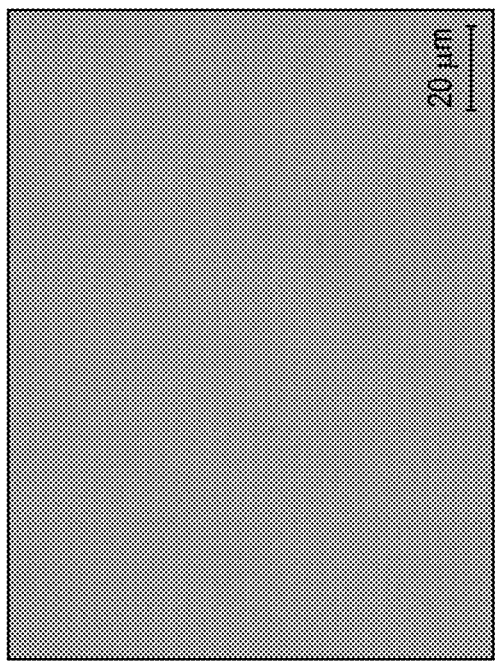

FIG. 13 shows the PSD and microscopy of the composited material both before and after filtration through a 10-micron polypropylene polishing filter. Filter was utilized for the removal of any larger particles. Filtration had no effect on the Particulate size distribution as seen in FIG. 14.

To mitigate particulate-any large particle if present post milling, a "polishing" filter, with a porosity small enough to retain larger particles, but not so small as to affect tegavivint assay is utilized. The four batches, prepared at the original test scale, were milled and composited. The nanosuspension composite was filtered through a 10-micron polypropylene (Pall HDCII), 10 micron. Initially, Pall Supor, 5 micron was used however filter clogging was observed. Then, Pall HDCII was used and showed no discernable impact on the particle-size distribution of the nanosuspension (as shown in FIGS. 13 and 14).

Example 4

Manufacturing a Lyophilized Formulation

The key focus of the manufacturing process was to obtain lyophilized formulation(s) that retained good cake integrity, re-suspended readily and demonstrated chemical stability over time. Nevertheless, freeze-thaw and suspension formulations of this milled material from the optimized milling process were also explored as alternative options. Additionally, some formulations were subjected to autoclaving prior to lyophilization, freeze-thaw or even for nanoparticle suspension formulations (prior to placing on stability) to determine the effect of a sterilization step on formulations. Autoclaved preparations were processed in bulk using a crimp-sealed serum bottle, which was heated to 121° C. or 20 minutes using a slow-release liquid cycle and allowed to equilibrate to ambient temperature before filling. Samples were filled at 0.5 mL into 2-mL serum bottles for testing.

Regardless of the starting crystal form, it was believed that autoclaving of the resulting nanosuspension of Form I would result in some additional annealing and improvement in the quality of suspended particles. The inventors believed that autoclaving may result in a small increase in the overall particle size that will still be in the range acceptable for IV dosing. Table 4 provides an overview of the different formulation preparations with and without autoclave treatment: For the formulation work, Form I (obtained from Form I as the starting material for milling at elevated temperature) was utilized.

TABLE 4

| Component | PSI ID 200529_For_006-A | PSI ID: 200529_For_006-B | PSI ID: 200529_For_006-C | PSI ID: 200529_For_006-D |
|---|---|---|---|---|
| [API]$_{final}$ | 25 mg/mL | 25 mg/ml | 50 mg/mL | 25 mg/mL |
| 200 mg/mL suspension | 1.5 mL | 1.5 mL | 5 mL | 6 mL |
| Sucrose | 1.2 g | — | — | — |
| Trehalose | — | 1.2 g | — | — |
| Sorbitol | — | — | 1.0 g | 2.4 g |
| WFI | qs. 12 mL | qs. 12 mL | qs. 20 mL | qs. 48 mL |
| Fill | 1 mL in 5 mL vial | 1 mL in 5 mL vial | 1 mL in 5 mL vial | 1 mL in 5 mL vial |
| No. of vials | 12 | 12 | 20 | 48 |
| Process | Suspension not autoclaved. Suspension subjected Lyophilization only | Suspension not autoclaved. Suspension subjected Lyophilization only. | Suspension Autoclaved. Suspension as is evaluated for stability. | Suspension not autoclaved prior to Freeze-thaw |

| Component | PSI ID: 200529_For_006-F | PSI ID: 200529_For_006-E | PSI ID: 200529_For_006-G |
|---|---|---|---|
| [API]$_{final}$ | 25 mg/mL | 25 mg/mL | 25 mg/mL |
| 200 mg/mL suspension | 6 mL | 6 mL | 6 mL |
| Sucrose | — | — | — |
| Trehalose | — | — | — |
| Sorbitol | 2.4 g | 2.4 g | 2.4 g |
| WFI | qs. 48 mL | qs. 48 mL | qs. 48 mL |
| Fill | 1 mL in 5 mL vial | 1 mL in 5 mL vial | 1 mL in 5 mL vial |
| No. of vials | 48 | 48 | 48 |
| Process | Suspension autoclaved prior to Freeze-thaw | Suspension not autoclaved, Suspension subjected Lyophilization only | autoclaved suspension prior to Lyophilization |

All the formulations containing the sorbitol had the same formulation composition with the exception of PSI ID: 200529_For_006-C which had double the concentration of API in the final concentration. The Sorbitol formulation with the final API concentration of 25 mg/mL were subjected to lyophilization (with or without autoclave) as well as freeze-thaw (with or without autoclave). Therefore, all formulations that evaluated the three different excipients were subjected to lyophilization.

The PSI ID: 200529_For_006-C formulation was subjected to autoclave treatment and placed on stability at 5° C. and 25° C. to evaluate the suspension stability as is, given the optimized milling process at elevated temperatures.

Preparation of Formulations:

The 20% (200 mg/mL) tegavivint poloxamer aqueous suspension was diluted with various potential cryoprotectant-containing diluents so that the final concentrations were 2.5% (25 mg/mL) tegavivint, 0.6% poloxamer, and the following:

Sucrose (10%)

Trehalose (10%)

Sorbitol (5%)

For the Formulation 200529_For_006-C

The 20% (200 mg/mL) tegavivint poloxamer aqueous suspension was diluted with potential cryoprotectant-containing diluents (sorbitol) so that the final concentrations were 5% (50 mg/mL) tegavivint, 1.25% poloxamer, and the following:

Sorbitol (5%)

Example 5

Pharmacokinetic Studies of Lyophilized Formulation and Nanosuspension Formulation This study was performed in overnight fasted (PO group) and non-fasted (IV group) Female Sprague-Dawley rats. Feed was provided to PO group rats 2 h post dose. BC2059 (tegavivint) Nanosuspension (Batch No. 61841790418A) and BC2059 Lyophilized (Batch No.: 210831_For_008) were the test items used in this study. Dose formulations were prepared on the day of treatment. 5% Dextrose in sterile water (Sterile D5W) was used as a vehicle for the preparation of IV and oral dose formulation.

The goal of this study was to determine the plasma pharmacokinetics and tissue distribution of BC2059 (two formulations) following a single dose IV infusion and oral administration in Female Sprague-Dawley rats.

TABLE 5

| Group allocation and treatment | | | | |
|---|---|---|---|---|
| Group | Treatment (Dose: mg/kg) | Animal ID No. | Dose Volume (mL/kg) | Formulation strength (mg/mL) | ROA |
| 1 | BC2059 Nanosuspension (31) | 1 to 12 | 2 | 15.5 | IV-infusion for 30 minutes |

TABLE 5-continued

Group allocation and treatment

| Group | Treatment (Dose: mg/kg) | Animal ID No. | Dose Volume (mL/kg) | Formulation strength (mg/mL) | ROA |
|---|---|---|---|---|---|
| 2 | BC2059 lyophilized formulation (31) | 13 to 24 | 2 | 15.5 | IV-infusion for 30 minutes |
| 3 | BC2059 lyophilized formulation (31) | 25 to 27 | 10 | 3.1 | PO |

Group 1 and 2 rats were administered intravenously (through Jugular vein via cannulation) for 30 minutes. The administration was a slow infusion by using Harvard Infusion pump at a flow rate of 66.67 µL/min delivering 2 mL over a period of 30 min. Potable water and feed was provided ad libitum to all animals. Each animal was mounted in metabolic cage during dose administration. Group 3 rats were administered orally via gavage. Blood samples were collected through retro orbital plexus puncture for PK sampling and cardiac puncture during sacrifice.

Blood and Tissue Samples Collection Schedule (from the End of Infusion):

|  | Group | | Time Points (h) | | | | | | |
|---|---|---|---|---|---|---|---|---|---|
|  | G1 | G2 | 0.083 | 0.5 | 1 | 2 | 4 | 8 | 24 |
| Rat IDs | 1 | 13 | X⁺ | | | | | | |
|  | 2 | 14 | X⁺ | | | | | | |
|  | 3 | 15 | X⁺ | | | | | | |
|  | 4 | 16 | | X⁺ | | | | | |
|  | 5 | 17 | | X⁺ | | | | | |
|  | 6 | 18 | | X⁺ | | | | | |
|  | 7 | 19 | | | | | X⁺ | | |
|  | 8 | 20 | | | | | X⁺ | | |
|  | 9 | 21 | | | | | X⁺ | | |
|  | 10 | 22 | X | X | X | X | X | X | X⁺ |
|  | 11 | 23 | X | X | X | X | X | X | X⁺ |
|  | 12 | 24 | X | X | X | X | X | X | X⁺ |

| Group | | Time Points (h) | | | | | |
|---|---|---|---|---|---|---|---|
| G3 | 0.083 | 0.5 | 1 | 2 | 4 | 8 | 24 |
| Rat IDs 25 | X | X | X | X | X | X | X⁺ |
| 26 | X | X | X | X | X | X | X⁺ |
| 27 | X | X | X | X | X | X | X⁺ |

X: Represents sampling through retro;
X⁺: Represents sampling through cardiac puncture and tissue collection At each PK sampling time points, ~0.2 mL of blood was withdrawn and 2 mL during scarification time point. Collected blood was transferred into a pre-labeled micro centrifuge tubes containing 200 mM $K_2$EDTA solution as anticoagulant and mixed gently by inverting the tube to facilitate mixing of anticoagulant with the blood. Following blood collection, animals were sacrificed by cervical dislocation and tissues [Brain, Heart, Kidneys (2), Liver, Lungs, Muscle (pectoral and thigh), Spleen and Visceral fat] were collected. Collected tissues were thoroughly washed with saline water. Blood samples were kept on ice bath until centrifugation. The collected blood samples were centrifuged at 4000 rpm for 10 min at 4° C. Plasma was separated after centrifugation. Plasma and tissues [Brain, Heart, Kidneys (2), Liver, Lungs, Muscle (pectoral and thigh), Spleen and Visceral fat] were transferred into pre-labeled (Study No., Animal ID No., Time point, Group and Matrix) tubes and stored at −70±10° C. until analysis.

Bioanalysis was performed using fit-for-purpose LC-MS/MS method for the quantification of BC2059 in plasma and tissue [Brain, Heart, Kidneys (2), Liver, Lungs, Muscle (pectoral and thigh), Spleen and Visceral fat] samples.

Results

The plasma and tissue pharmacokinetic parameters for BC2059 were calculated using standard non-compartmental analysis (Phoenix® software, version 8.3, Pharsight Corporation, Mountain View, California 94040/USA) using linear trapezoidal method with linear interpolation.

PK parameters for group 3 on oral administration of BC2059 lyophilized formulation (31 mg/kg) were not calculated due to insufficient significant concentrations.

No clinical signs and no mortality/no morbidity were observed in all treated group animals at tested dose.

The plasma and tissue pharmacokinetic parameters of BC2059 were evaluated by treatment with one formulation of BC2059 Nanosuspension (Group 1) and two formulations of BC2059 lyophilized formulation (Group 2 and Group 3) following a single IV-infusion or oral route of administration in Female Sprague-Dawley rats. Values are expressed as Mean and n=3 rats/time point.

The plasma and tissue concentrations were determined in Female Sprague-Dawley rats at 31 mg/kg over the period of 24 hr. The plasma and tissue exposures ($C_{max}$ and $AUC_{last}$) were found higher in group 2 when compared to group 1. The plasma exposure levels, $C_{max}$ and $AUC_{last}$ were found to be 9-folds and 3.8-folds higher, respectively in group 2 when compared to group 1. Distribution to various tissues was found to be higher in group 2 when compared with that of group 1.

For BC2059 in group 1, the order of exposures ($C_{max}$) was Liver>Spleen>Lungs>Plasma>Kidney>Heart>Visceral fats>Muscles>Brain.

For BC2059 in group 1, the order of exposures ($AUC_{last}$) was Liver>Spleen>Lungs>Kidney>Heart>Plasma>Visceral fats>Muscles>Brain.

For BC2059 in group 2, the order of exposures ($C_{max}$) was Spleen>Liver>Plasma>Lungs>Kidney>Heart>Visceral fats>Muscles>Brain.

For BC2059 in group 2, the order of exposures ($AUC_{last}$) was Spleen>Liver>Lungs>Plasma>Kidney>Heart>Visceral fats>Muscles>Brain

TABLE 6

Arithmetic mean Plasma Pharmacokinetic parameters of BC2059 following a single IV-infusion or oral administration of BC2059 Nanosuspension to Female Sprague-Dawley Rats (Group 1: 31 mg/kg)

| PK parameters | Plasma | Brain | Heart | Kidney | Lungs | Muscle (pectoral, thigh) | Spleen | Visceral fat | Liver |
|---|---|---|---|---|---|---|---|---|---|
| $C_{max}$ (ng/mL for plasma and ng/g for tissues) | 5770 | 119 | 2450 | 2550 | 17700 | 151 | 219000 | 293 | 251000 |

TABLE 6-continued

Arithmetic mean Plasma Pharmacokinetic parameters of BC2059 following a single IV-infusion or oral administration of BC2059 Nanosuspension to Female Sprague-Dawley Rats (Group 1: 31 mg/kg)

| PK parameters | Plasma | Brain | Heart | Kidney | Lungs | Muscle (pectoral, thigh) | Spleen | Visceral fat | Liver |
|---|---|---|---|---|---|---|---|---|---|
| $T_{max}$ (hr) | 0.083 | 0.5 | 4 | 4 | 4 | 24 | 4 | 24 | 0.5 |
| $AUC_{last}$ (hr · ng/mL for plasma and hr · ng/g for tissues) | 18000 | 1250 | 34700 | 39700 | 275000 | 3420 | 3620000 | 3790 | 4340000 |

Note:
Values are expressed as Mean

TABLE 7

Arithmetic mean Plasma Pharmacokinetic parameters of BC2059 following a single IV-infusion or oral administration of BC2059 lyophilized formulation to Female Sprague-Dawley Rats (Group 2: 31 mg/kg)

| PK parameters | Plasma | Brain | Heart | Kidney | Lungs | Muscle (pectoral, thigh) | Spleen | Visceral fat | Liver |
|---|---|---|---|---|---|---|---|---|---|
| $C_{max}$ (ng/mL for plasma and ng/g for tissues) | 53700 | 204 | 2900 | 3760 | 35700 | 403 | 36700 | 475 | 237000 |
| $T_{max}$ (hr) | 0.083 | 0.5 | 1 | 0.5 | 0.5 | 0.5 | 0.5 | 1 | 1 |
| $AUC_{last}$ (hr · ng/mL for plasma and hr · ng/g for tissues) | 68500 | 1890 | 45300 | 58500 | 459000 | 5790 | 4850000 | 4160 | 3610000 |
| $AUC_{int\_obs}$ (hr · ng/mL for plasma and hr · ng/g for tissues) | 75500 | | | | | NA | | | |
| $AUC_{temp\_obs}$(%) | 9.23 | | | | | | | | |
| $K_{el}$(1/hr) | 0.074 | | | | | | | | |
| $T_{1/2}$ (hr) | 9.37 | | | | | | | | |
| Cl//F (mL/min/kg) | 6.84 | | | | | | | | |
| $V_{SS}$(L/kg) | 2.77 | | | | | | | | |
| $MRT_{last}$ (hr) | 3.65 | | | | | | | | |

Note:
Values are expressed as Mean; NA; Not Applicable

These data are also illustrated in FIGS. 31-35.

Figure 31:
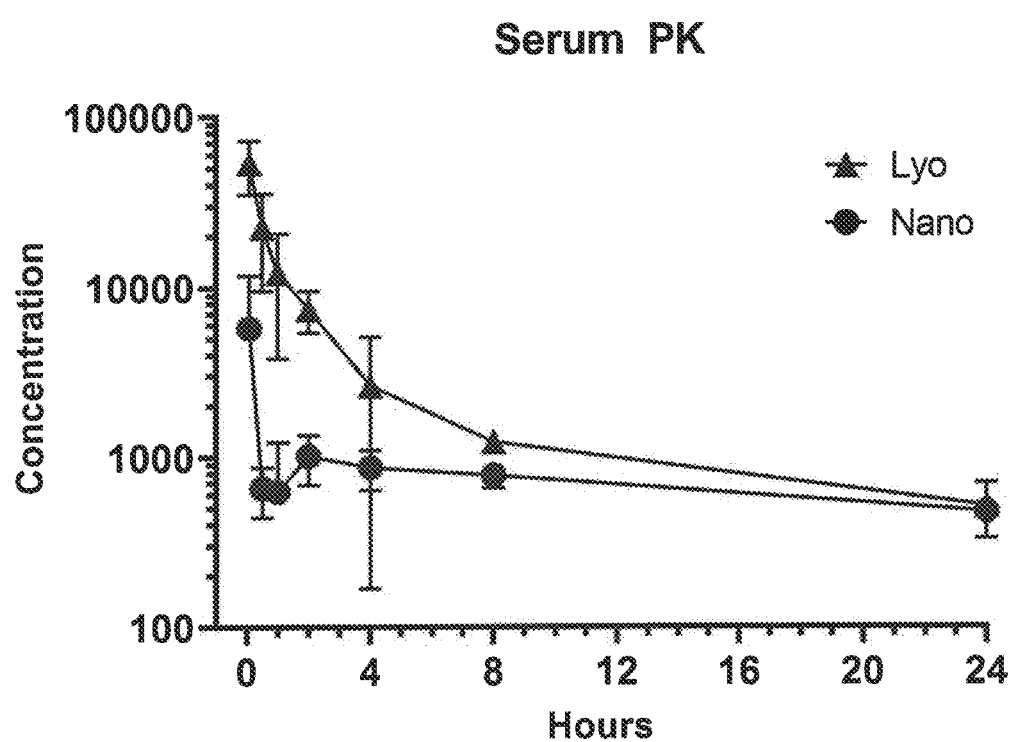
FIG. 31 is a plot of serum concentration of tegavivint vs time of a lyophilized formulation and a non-lyophilized formulation.

FIG. 31 is a plot of serum concentration of tegavivint vs time of a lyophilized formulation and a non-lyophilized formulation. As one can see, administration of a lyophilized formulation resulted in higher serum concentrations of tegavivint starting from hour 0 and through hour 24.

Figure 32:
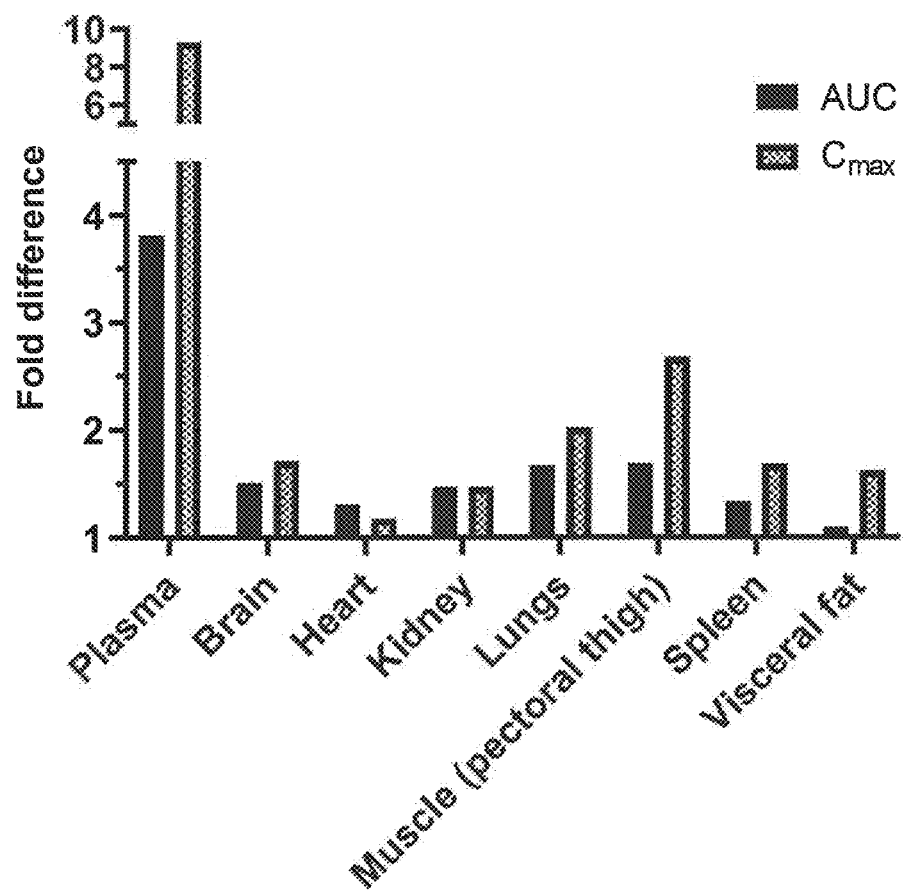
FIG. 32 is a bar chart of $AUC_{last}$ and $C_{max}$ values of a lyophilized formulation and a non-lyophilized formulation of tegavivint.

FIG. 32 is a bar chart of $AUC_{last}$ and $C_{max}$ values of a lyophilized formulation and a non-lyophilized formulation of tegavivint. The lyophilized formulation has resulted in higher values of both $AUC_{last}$ and $C_{max}$ across various tissues.

Figure 33:
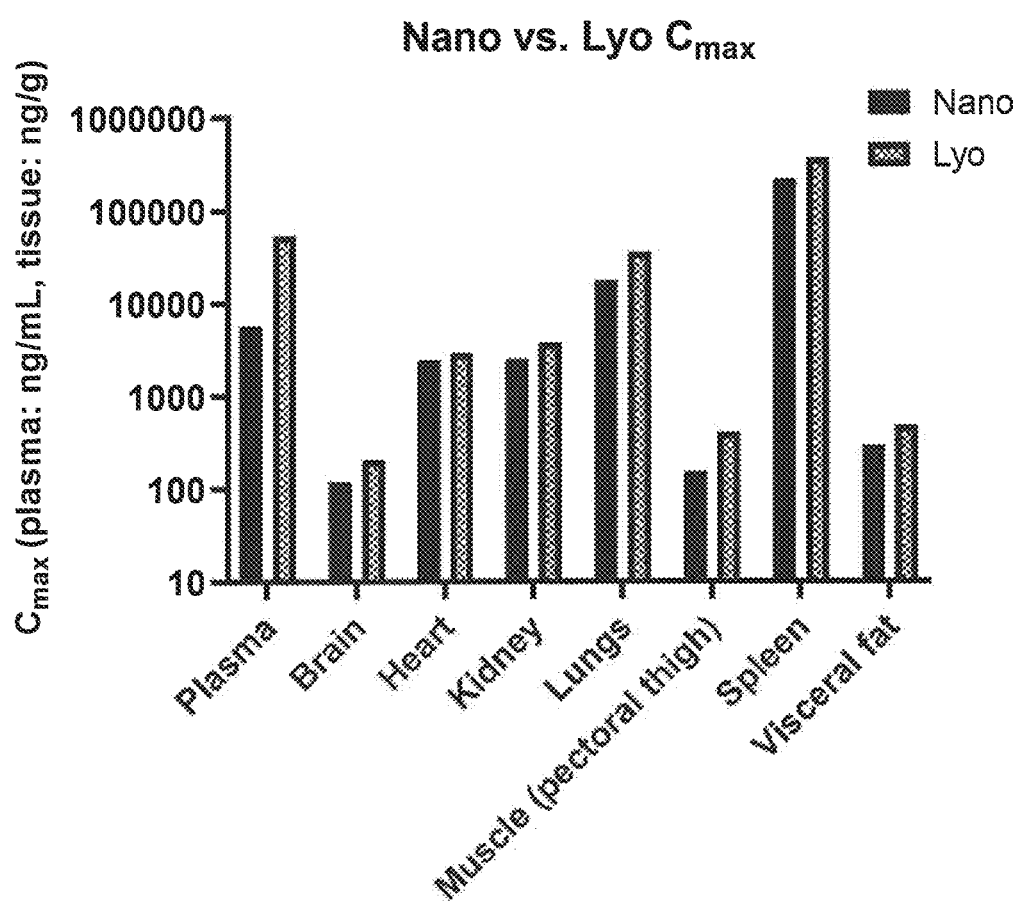
FIG. 33 is a bar chart of $C_{max}$ values of a lyophilized formulation and a non-lyophilized formulation of tegavivint.

FIG. 33 is a bar chart of $C_{max}$ values of a lyophilized formulation and a non-lyophilized formulation of tegavivint. The lyophilized formulation has resulted in higher $C_{max}$ values across various tissues.

Figure 34:
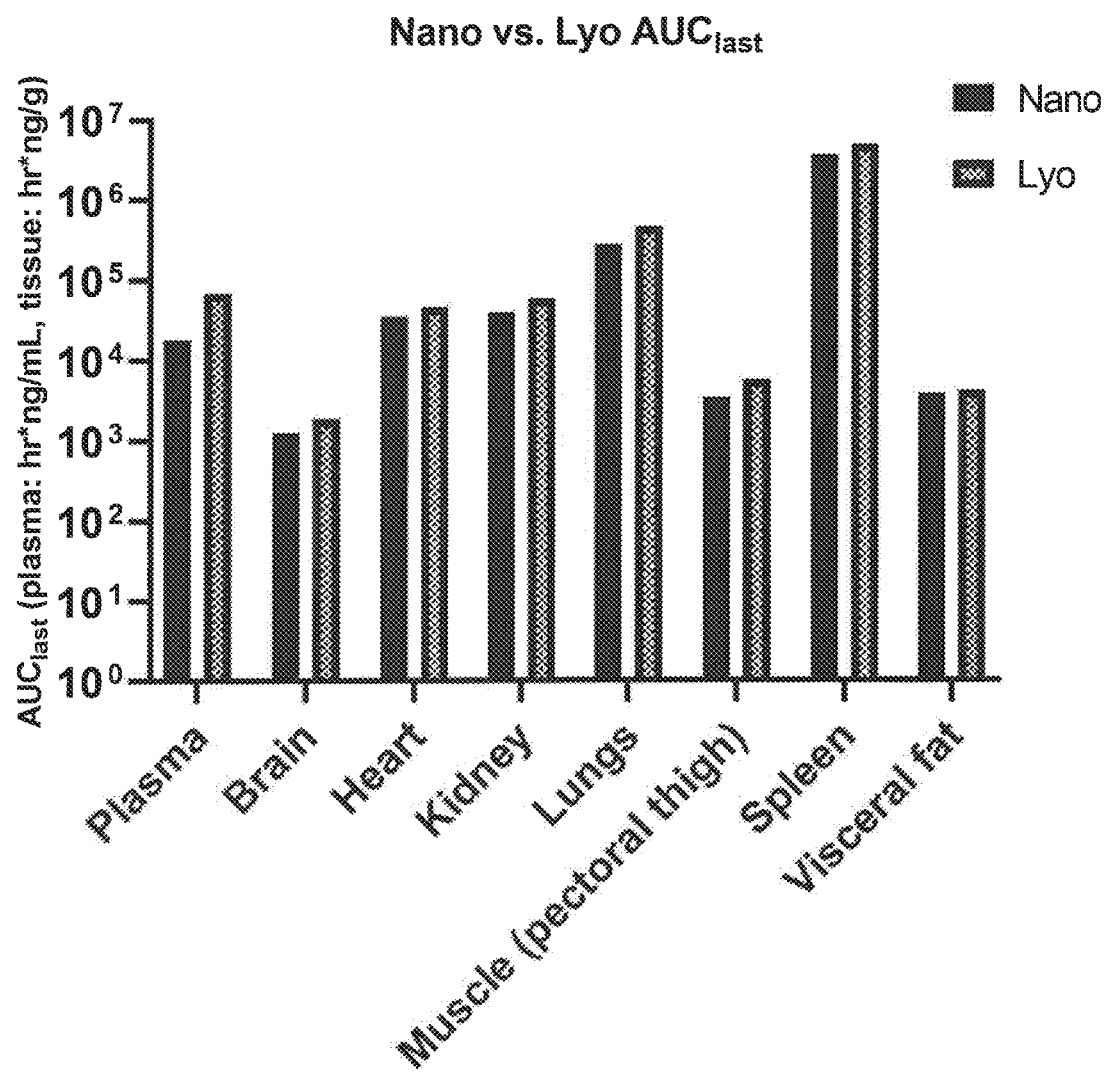
FIG. 34 is a bar chart of $AUC_{last}$ values of a lyophilized formulation and a non-lyophilized formulation of tegavivint.

FIG. 34 is a bar chart of $AUC_{last}$ values of a lyophilized formulation and a non-lyophilized formulation of tegavivint. The lyophilized formulation has resulted in higher $AUC_{last}$ values across various tissues.

Figure 35:
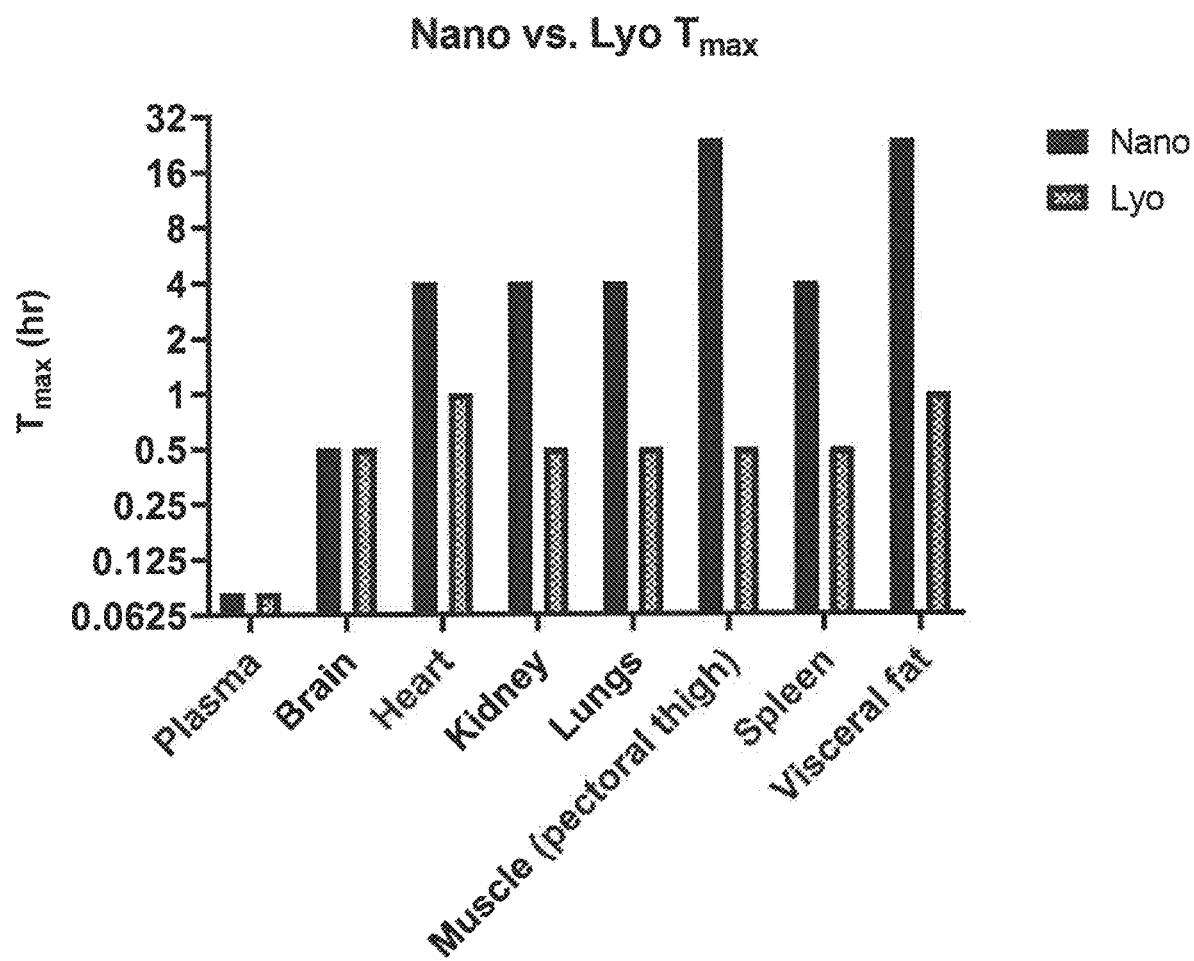
FIG. 35 is a bar chart of $T_{max}$ values of a lyophilized formulation and a non-lyophilized formulation of tegavivint.

FIG. 35 is a bar chart of $T_{max}$ values of a lyophilized formulation and a non-lyophilized formulation of tegavivint. The lyophilized formulation has resulted in lower $T_{max}$ time values across various tissues.

Additional Information on Materials and Equipment Used in Examples

Excipients
Poloxamer 188: Spectrum and BASF
Sucrose: Spectrum
Trehalose: EMD Millipore
Sorbitol: VWR
Supplies
Milling media: SSDP Polystyrene Grinding Media, 0.4-0.6 mm
Equipment
Vertical mill: custom design batch mill
Particle-size analyzer: Horiba LA-960
Microscope: Leica DMRB and Olympus BX51
Differential Scanning Calorimeter: Mettler-Toledo DSC-1
Lyophilization Parameters:
Lyophilized preparations were dried according to the recipe outlined below.
Overview of Lyophilization: modified cycle:
  Frozen to −40° C. (120 min final hold);
  No annealing;
  Primary drying at −30° C./100 mTorr (1440 min);
  Secondary drying at −10° C./200 mTorr (720 min);

Ramp to storage at 25° C./200 mTorr.

| Stage | Shelf Temperature | Ramp Time | Hold Time | Pressure |
|---|---|---|---|---|
| Freezing | 20° C. | 0 min | 5 min | N/A |
|  | 5° C. | 30 min | 0 min | N/A |
|  | 5° C. | 0 min | 30 min | N/A |
|  | −5° C. | 240 min | 0 min | N/A |
|  | −5° C. | 0 min | 5 min | N/A |
|  | −40° C. | 60 min | 0 min | N/A |
|  | −40° C. | 0 min | 120 min | N/A |
| Primary Drying | −40° C. | 0 min | 5 min | 100 mTorr |
|  | −30° C. | 20 min | 0 min | 100 mTorr |
|  | −30° C. | 0 min | 720 min | 100 mTorr |
|  | −30° C. | 0 min | 720 min | 100 mTorr |
| Secondary Drying | −10° C. | 90 min | 0 min | 200 mTorr |
|  | −10° C. | 0 min | 720 min | 200 mTorr |
| Storage | 25° C. | 30 min | 0 min | 200 mTorr |
|  | 25° C. | 0 min | 5 min | 200 mTorr |

All formulations subjected to lyophilization, freeze thaw and suspension (milled preparation as is post autoclave treatment) were subjected to initial testing (T0).

Figure 15:
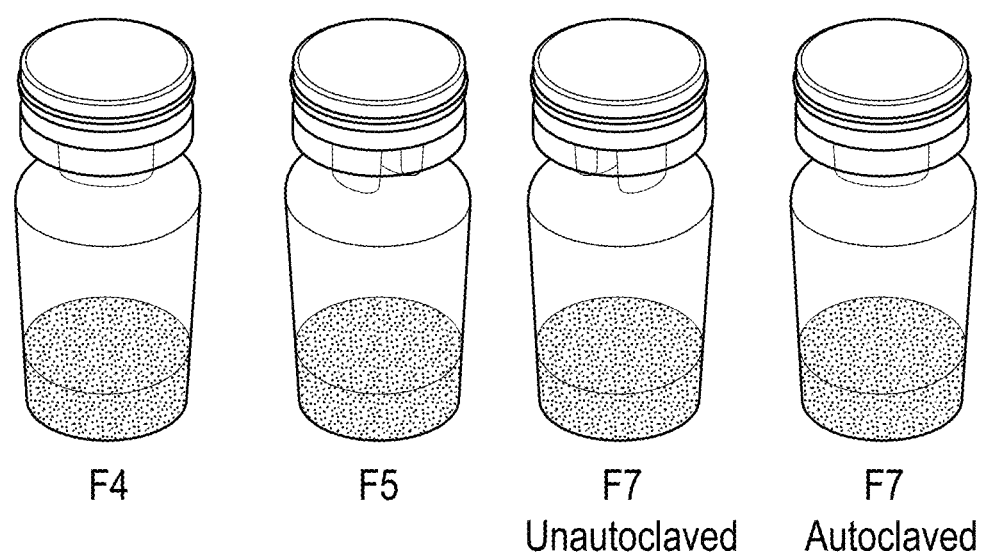
FIG. 15 a picture of lyophilized vials with formulations of the invention.

Lyophilized vials, examples of which are shown in FIG. 15, showed uniform, well-developed cake structure with negligible shrinkage.

FIG. 15 depicts lyophilized vials as follows:
F4 equates to 200529_For_006-A
F5 equates to 200529_For_006-B
F7 (un autoclaved) equates to 200529_For_006-E
F7 (Autoclaved) equates to 200529_For_006-G.

De-ionized water was used as a diluent for reconstitution of the lyophilized formulations.

All initial PSD data and microscopy on reconstitution showed no appreciable change from the pre-treatment data.

All lyophilized formulations resuspended readily and met PSD and OM criteria. Assay/Relative Substance testing showed no impact on chemical stability post lyophilization.

| Sample | Lyophilized | Autoclaved | % LC & Amount | Total Impurities |
|---|---|---|---|---|
| 2002283-1-25 mg/g Tegavivint with sucrose | No | Yes | 104.5%, 26.1 mg | 0.62% |
| 2002283-2-25 mg/g Tegavivint with trehalose | No | Yes | 105.2%, 26.3 mg | 0.67% |
| 2002283-3-50 mg/g Tegavivint with sorbitol | Yes | No | 96.7%, 48.3 mg | 0.61% |
| 2002283-4-25 mg/g Tegavivint with sorbitol | No | No | 95.0%, 23.8 mg | 0.54% |
| 2002283-5-25 mg/g Tegavivint with sorbitol | No | Yes | 106.1%, 26.5 mg | 0.59% |
| 2002283-6-25 mg/g Tegavivint with sorbitol | Yes | No | 94.9%, 23.7 mg | 0.55% |
| 2002283-7-25 mg/g Tegavivint with sorbitol | Yes | Yes | 105.1%, 26.3 mg | 0.61% |

Results are averages of n=3

Freeze thaw cycle for non-autoclaved vials showed no clumps under microscopy after 1 cycle (Freeze at −20° C. and thaw at room temperature after 1-2 days).

Figure 16:
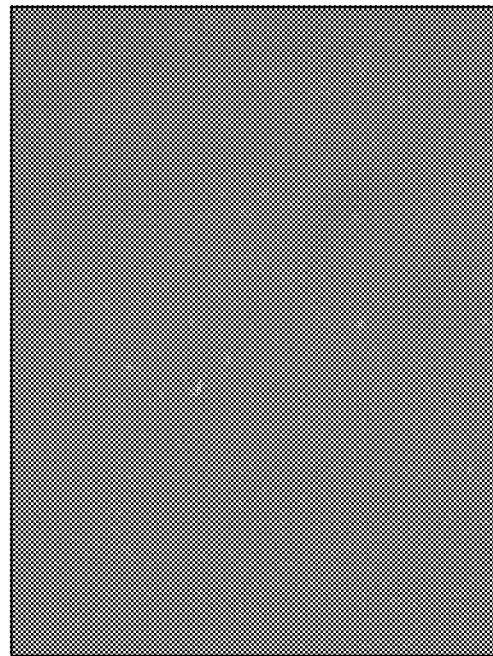
FIG. 16 is an optical microscopy image of one of the inventive formulations.
Figure 16:
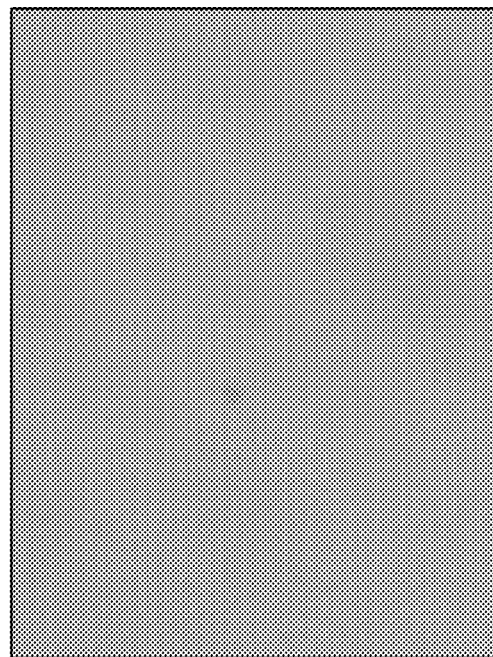

FIG. 16 is Freeze/Thaw Microscopy of 200529_For_006-D (400×, bright-field and polarized)-non-autoclaved.

Lyophilized formulations were placed on stability under two different conditions (5° C. and 25° C.) and stability analyses are being performed at 3M, 6M, 12M (optional) and 18M (optional). For the freeze thaw study, samples are being held frozen at −20° C. for six months followed by thawing and analysis. For the suspension formulations, stability analyses are being performed at T6M, T12M and T18 months (optional).

The observations from recent analysis of the T3M testing of the lyophilized formulations are as follows:

All four lyophilized formulations (from both 5° C. and 25° C.) showed good cake integrity at the end of T3M; Figures below show lyophilized vials at T3M pre- and post-rehydration.

Figure 17:
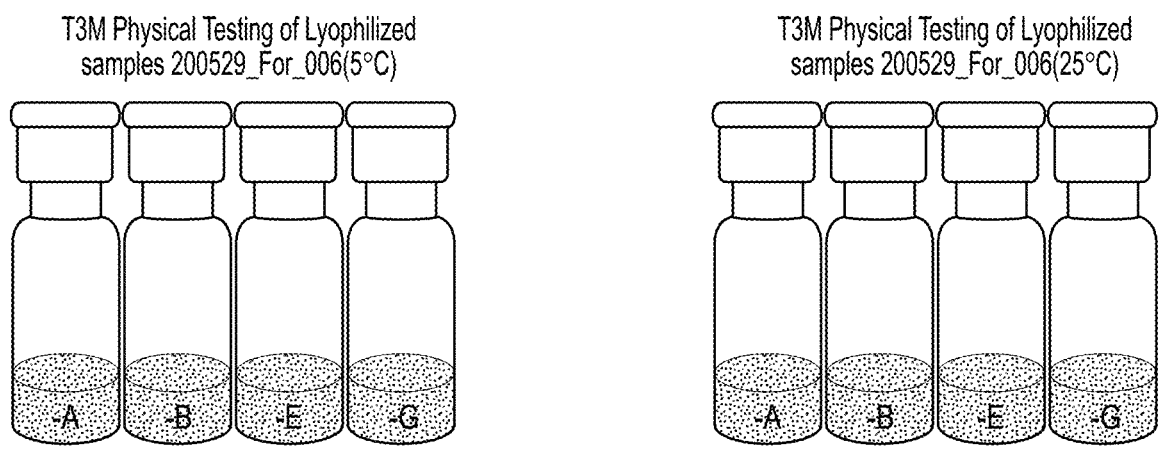
FIG. 17 is a picture of lyophilized vials with formulations of the invention prior to rehydration.
Figure 18:
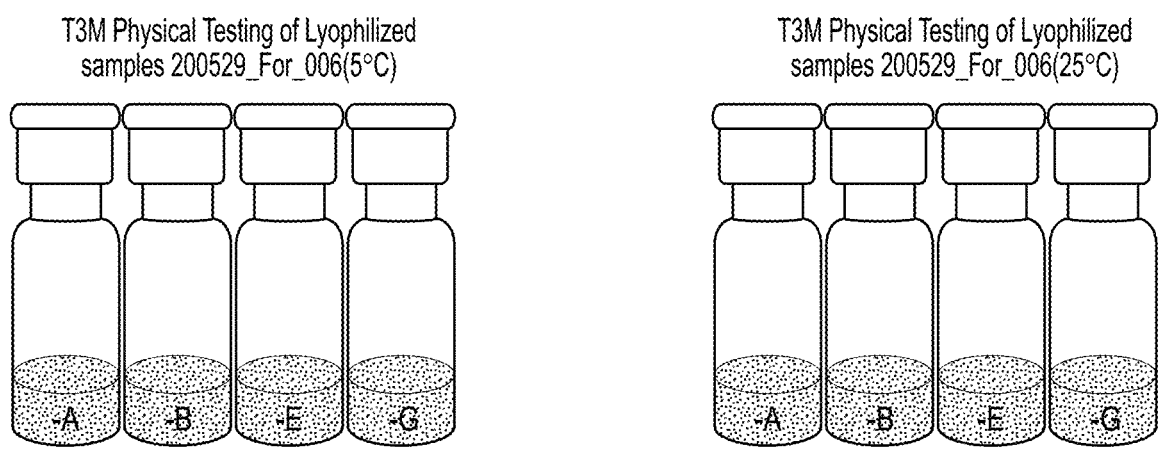
FIG. 18 is a picture of lyophilized vials with formulations of the invention after rehydration.
Figure 19:
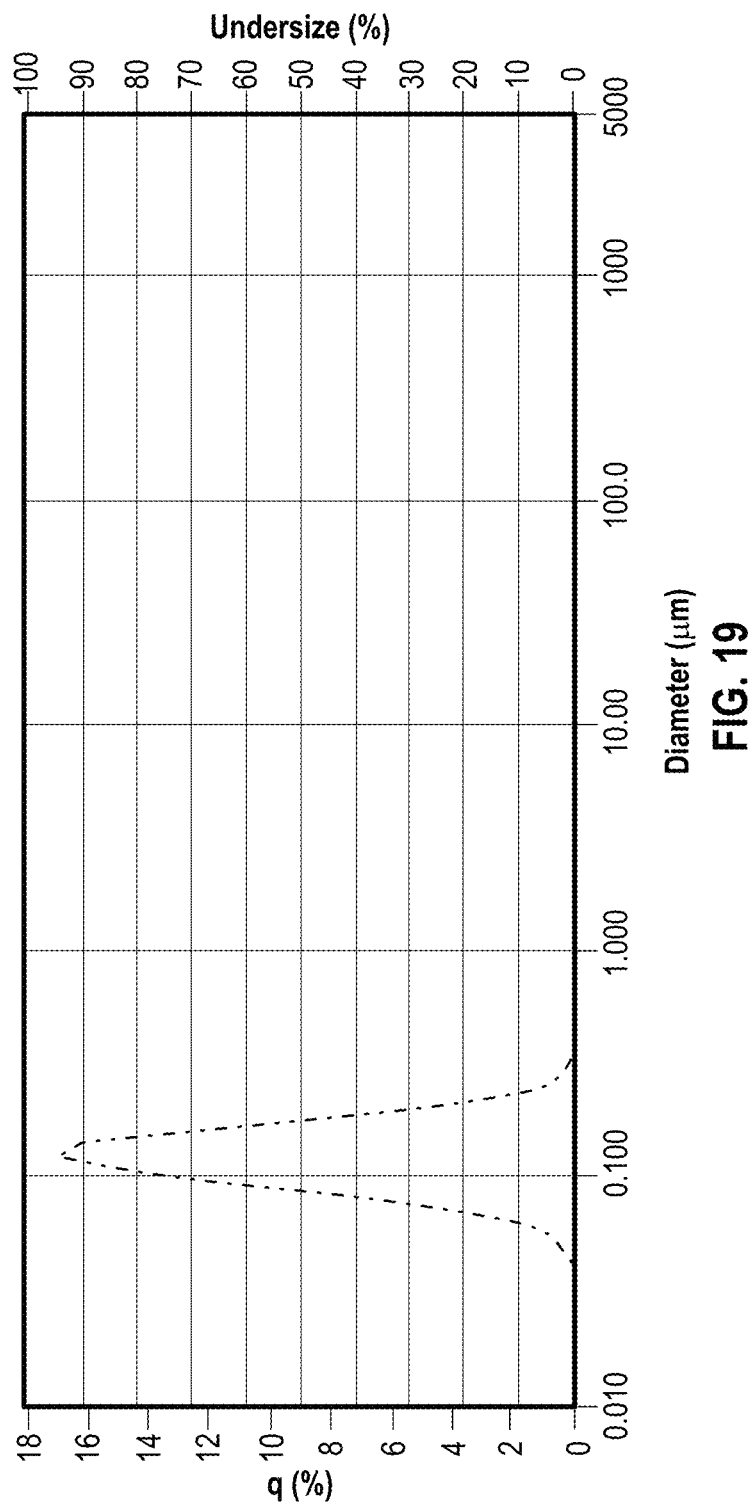
FIG. 19 is a PSD overlay of another inventive formulation.

FIG. 17 shows lyophilized vials prior to rehydration.
FIG. 18 shows lyophilized vials after rehydration.
All lyophilized formulations were readily reconstituted; and
Particulate size distribution profile between 5° C. and 25° C. for each of the formulations overlap (except for F7 autoclaved which exhibited a slight PSD shift possibly as a result of autoclaving). The PSD and Optical microscopy images of the reconstituted samples for each of the lyophilized formulation is presented in FIG. 19.

Figure 20:
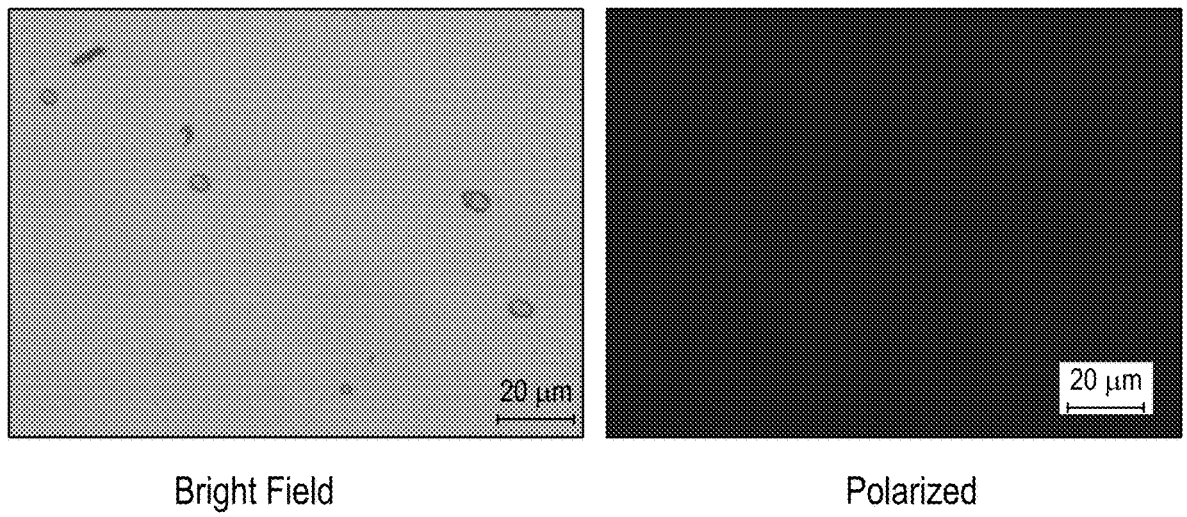
FIG. 20 is an optical microscopy image of one of the inventive formulations.

FIG. 20 shows microscopy images of 10% sucrose batch (T3M @5° C., 400×). The left panel is Bright Field. The right panel is Polarized.

Figure 21:
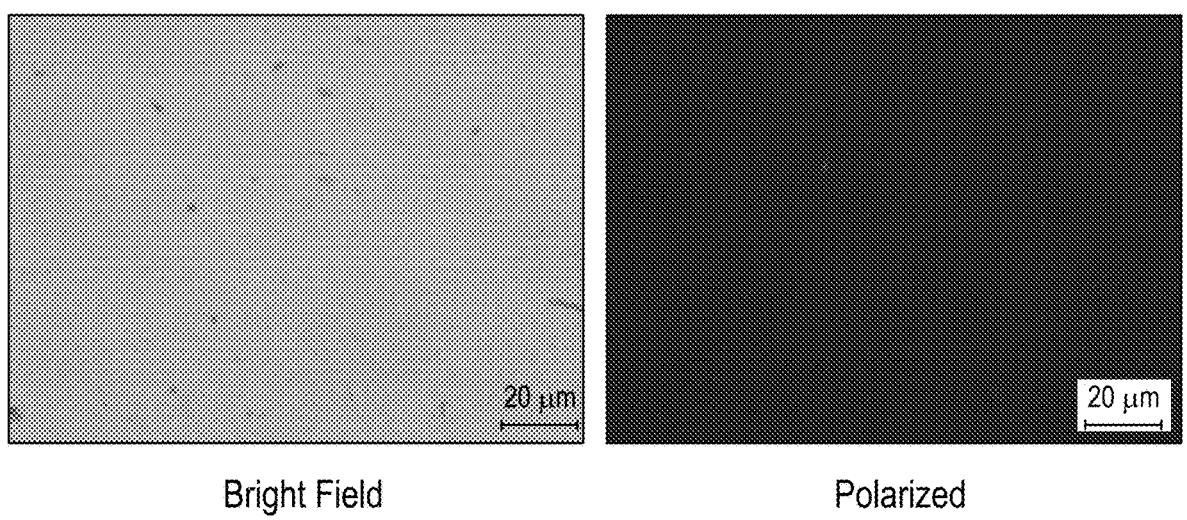
FIG. 21 is an optical microscopy image of one of the inventive formulations.

FIG. 21 shows microscopy images of 10% sucrose batch (T3M @25° C., 400×). The left panel is Bright Field. The right panel is Polarized.

Figure 22:
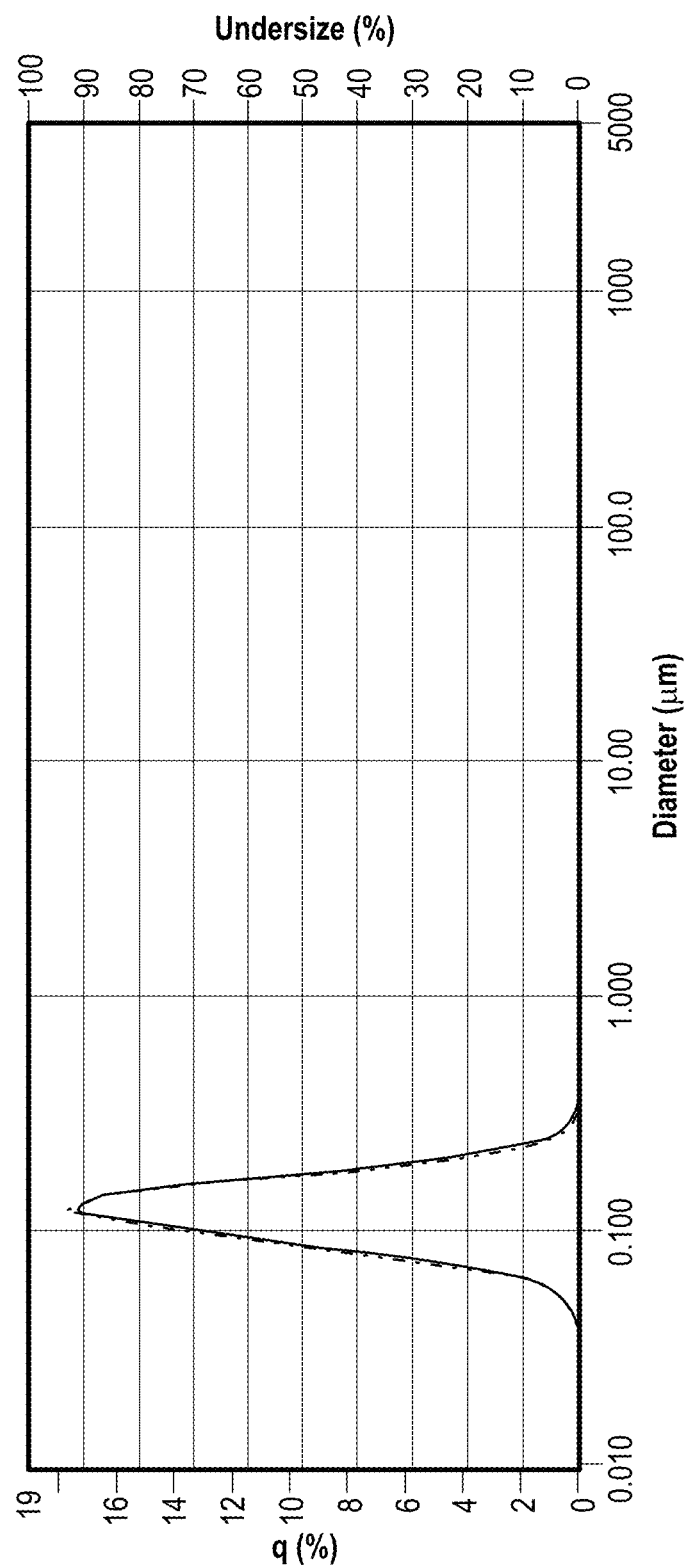
FIG. 22 is a PSD overlay of another inventive formulation.

FIG. 22 shows a PSD Data Overlay for 10% trehalose batch (T3M @ 5° C. and 25° C.)

Figure 23:
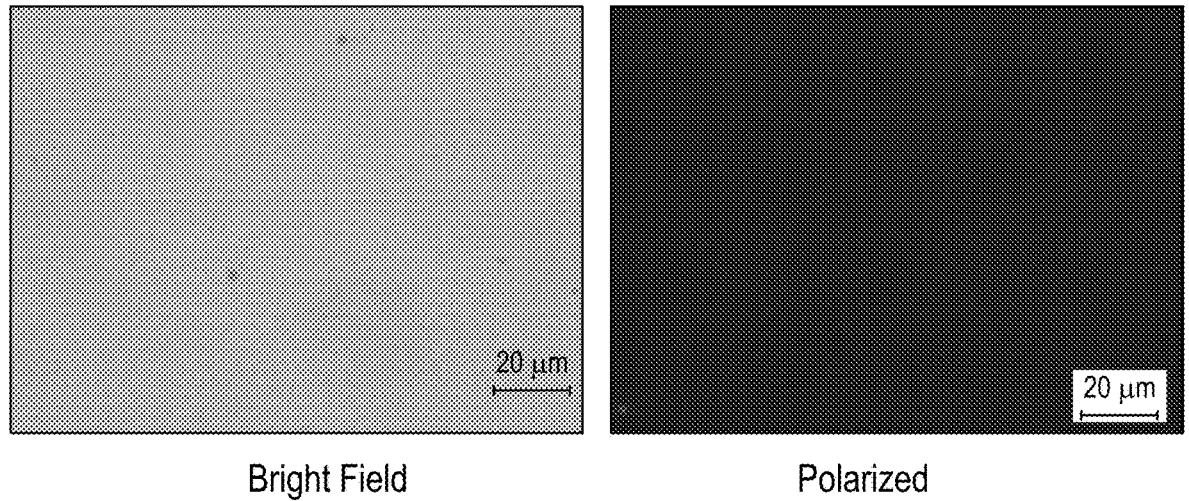
FIG. 23 is an optical microscopy image of one of the inventive formulations.

FIG. 23 shows microscopy images of 10% trehalose batch (T3M @5° C., 400×). The left panel is Bright Field. The right panel is Polarized.

Figure 24:
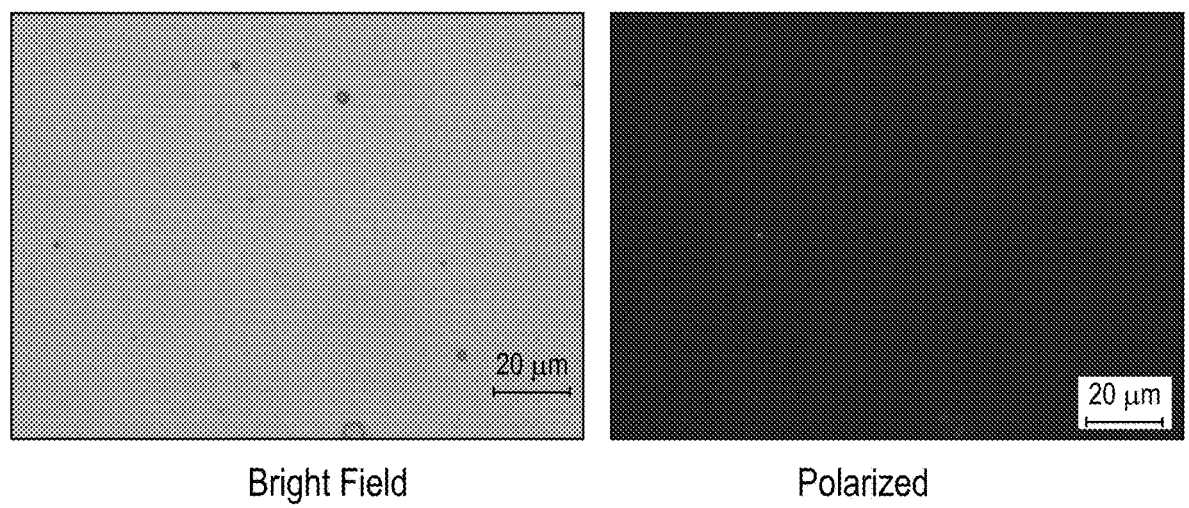
FIG. 24 is an optical microscopy image of one of the inventive formulations.

FIG. 24 shows microscopy images of 10% trehalose batch (T3M @25° C., 400×). The left panel is Bright Field. The right panel is Polarized.

Figure 25:
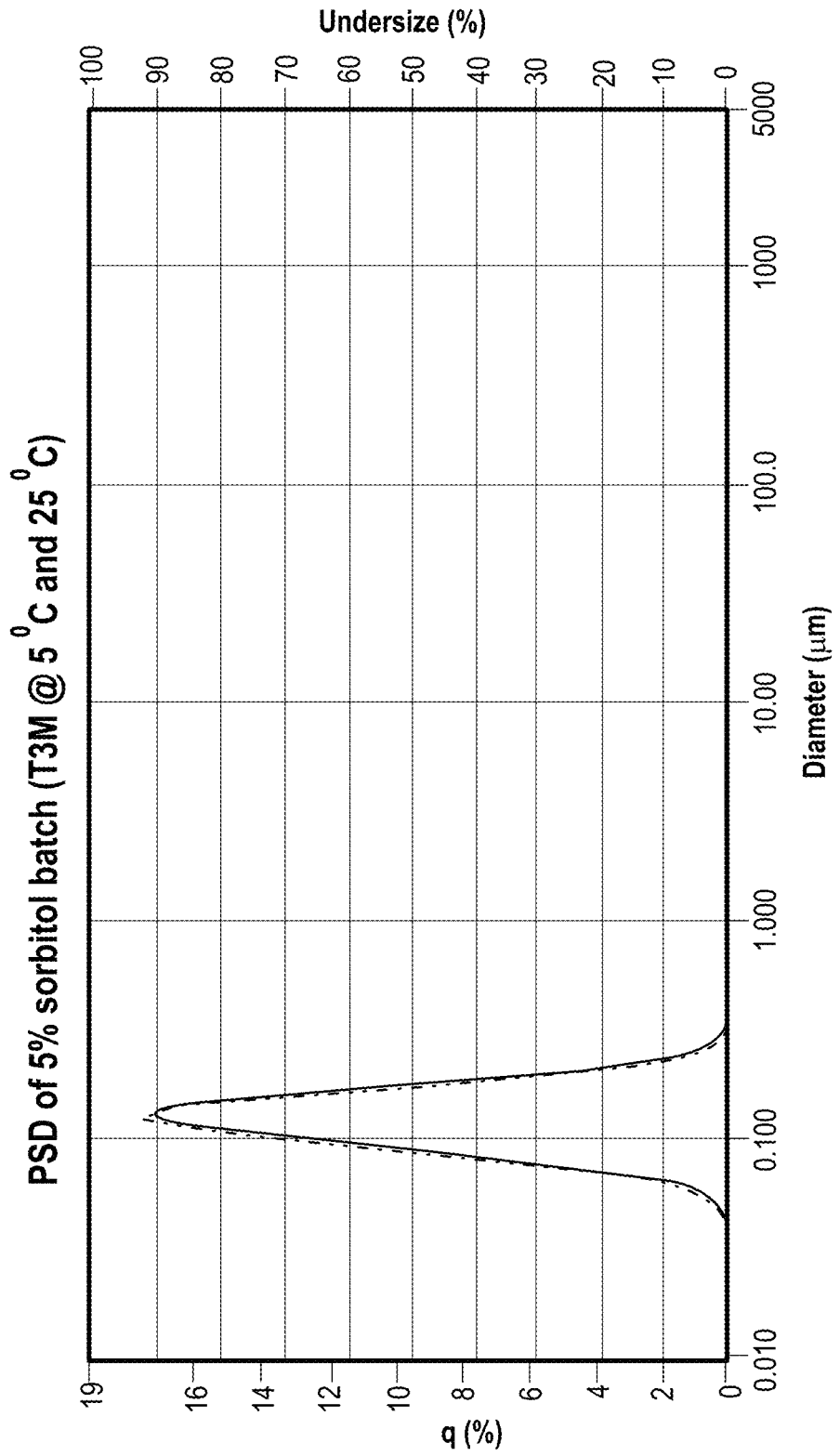
FIG. 25 is a PSD overlay of another inventive formulation.

FIG. 25 shows a PSD Data Overlay for 5% sorbitol batch (T3M @ 5° C. and 25° C.).

Figure 26:
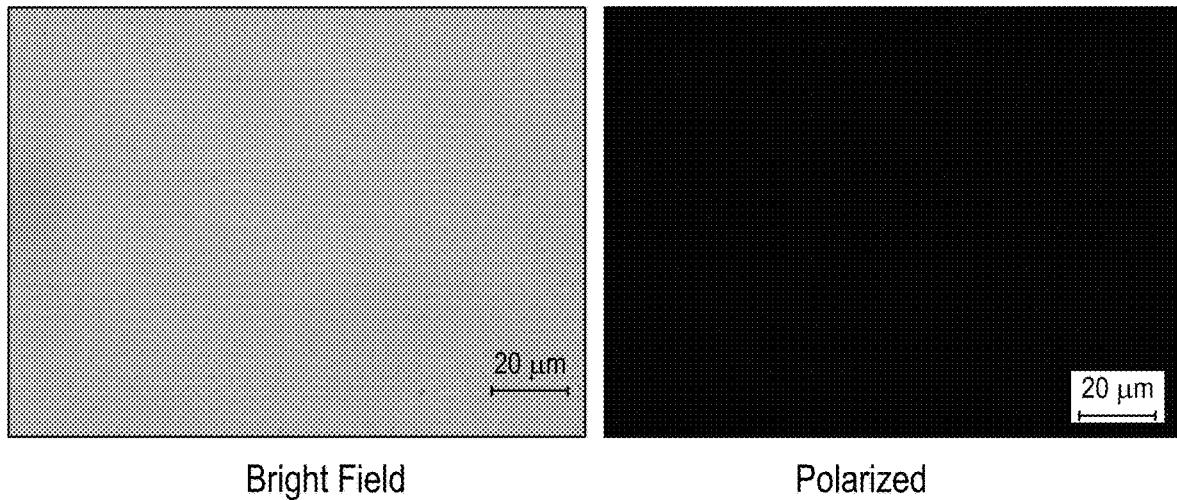
FIG. 26 is an optical microscopy image of one of the inventive formulations.

FIG. 26 shows microscopy images of 5% sorbitol batch (T3M @5° C., 400×). The left panel is Bright Field. The right panel is Polarized.

Figure 27:
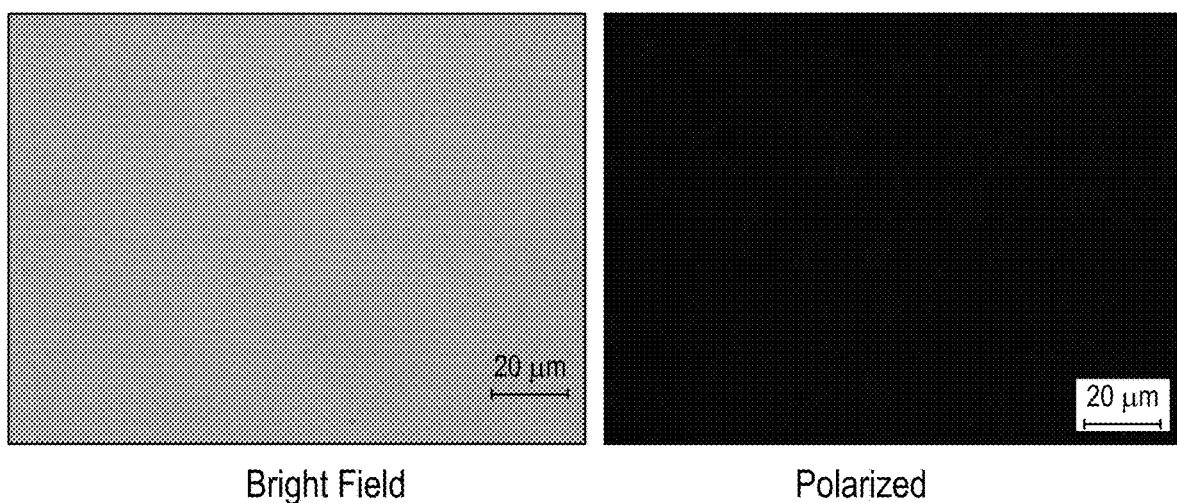
FIG. 27 is an optical microscopy image of one of the inventive formulations.

FIG. 27 shows microscopy images of 5% sorbitol batch (T3M @25° C., 400×). The left panel is Bright Field. The right panel is Polarized.

Figure 28:
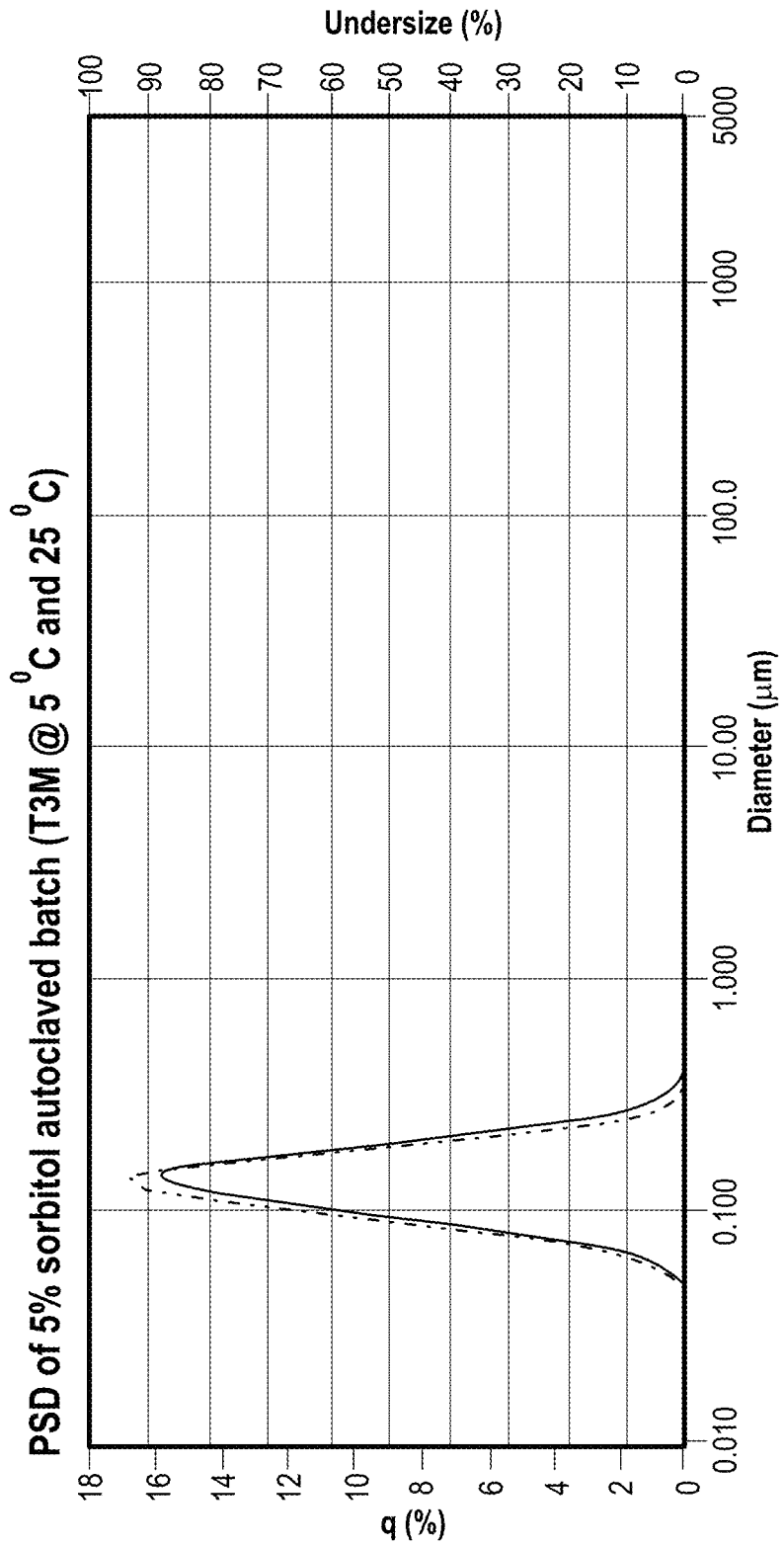
FIG. 28 is a PSD overlay of another inventive formulation.

FIG. 28 shows a PSD Data Overlay for 5% sorbitol autoclaved batch (T3M @ 5° C. and 25° C.).

Figure 29:
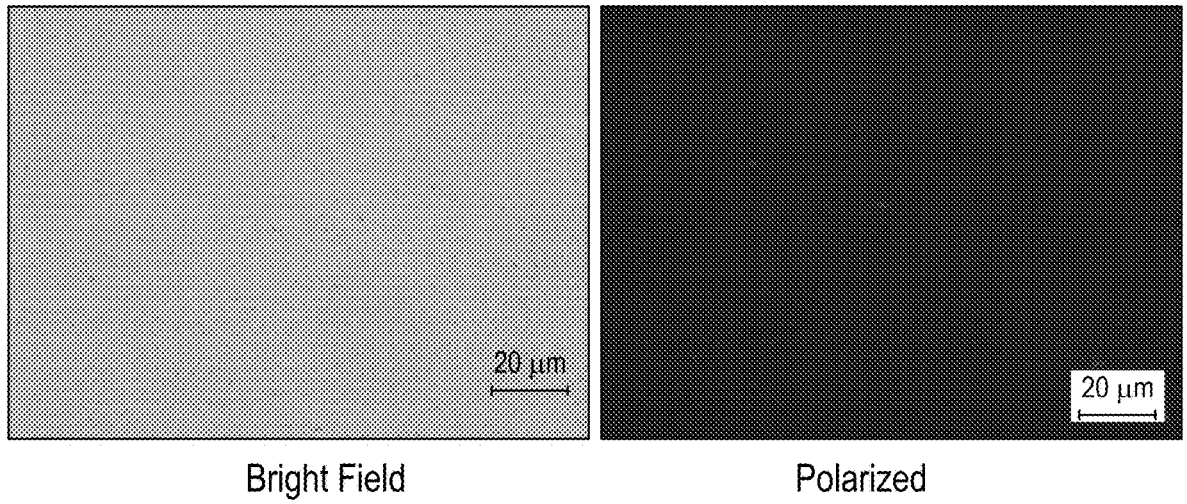
FIG. 29 is an optical microscopy image of one of the inventive formulations.

FIG. 29 shows microscopy images of 5% sorbitol autoclaved batch (T3M @5° C., 400×). The left panel is Bright Field. The right panel is Polarized.

Figure 30:
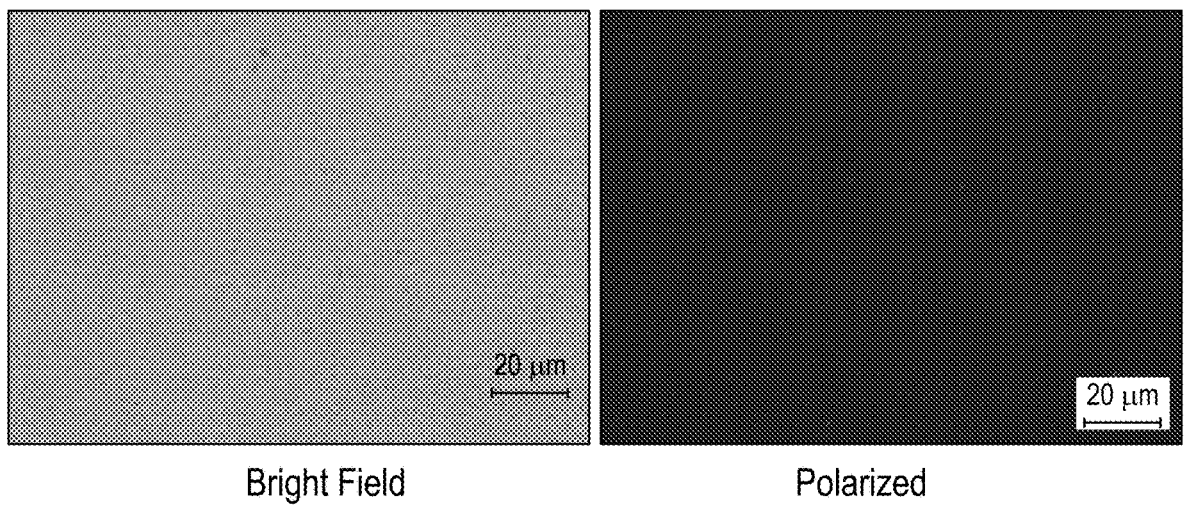
FIG. 30 is an optical microscopy image of one of the inventive formulations.

FIG. 30 shows microscopy images of 5% sorbitol autoclaved batch (T3M @25° C., 400×). The left panel is Bright Field. The right panel is Polarized.

What is claimed is:

1. A formulation comprising particles of Form I or Form IV polymorph of tegavivint or a pharmaceutically acceptable salt thereof; wherein 90% of particles have a diameter (D90) of less than or equal to 0.2 micron when measured using laser diffraction, wherein the formulation comprises a poloxamer, and one or more stabilizers selected from the group consisting of sucrose, trehalose and sorbitol and wherein the formulation was prepared by high energy agitator milling at a temperature of between about 40° C. and about 60° C.

2. The formulation of claim 1, wherein 50% of particles have a diameter (D50) of less than or equal to 0.12 micron when measured using laser diffraction.

3. The formulation of claim 1, wherein 10% of particles have a diameter (D10) of less than or equal to 0.1 micron when measured using laser diffraction.

4. The formulation of claim 1, wherein the formulation is anhydrous.

5. The formulation of claim 1, wherein the formulation is stable for three months during a storage at a temperature of between 5° C. and 25° C.

6. The formulation of claim 1, wherein the formulation is stable for six months during a storage at a temperature of between 5° C. and 25° C.

7. The formulation of claim 1, wherein the formulation is stable for twelve months during a storage at a temperature of between 5° C. and 25° C.

8. The formulation of claim 1, wherein the formulation is stable for eighteen months during a storage at a temperature of between 5° C. and 25° C.

9. The formulation of claim 8, wherein tegavivint concentration is between 25 mg/mL and 50 mg/mL.

10. The formulation of claim 1, wherein the poloxamer concentration is between 6 mg/mL and 12 mg/mL.

11. The formulation of claim 1, wherein the poloxamer concentration is 6 mg/mL.

12. The formulation of claim 1, wherein the poloxamer concentration is 12.5 mg/mL.

13. The formulation of claim 1, wherein the sorbitol concentration is 50 mg/mL.

14. The formulation of claim 1, wherein the tegavivint is Form I polymorph.

15. The formulation of claim 1, wherein the tegavivint is Form IV polymorph.

16. A method for treating cancer or tumor metastasis in a mammal in need thereof comprising administering to said mammal an effective amount of the formulation according to claim 1.

* * * * *